US011983872B2

(12) United States Patent
Endo

(10) Patent No.: US 11,983,872 B2
(45) Date of Patent: May 14, 2024

(54) MEDICAL IMAGE PROCESSING DEVICE, OPERATION METHOD OF MEDICAL IMAGE PROCESSING DEVICE, AND NON-TRANSITORY COMPUTER READABLE MEDIUM

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/302,579

(22) Filed: Apr. 18, 2023

(65) Prior Publication Data

US 2023/0274429 A1 Aug. 31, 2023

Related U.S. Application Data

(63) Continuation of application No. PCT/JP2021/033822, filed on Sep. 15, 2021.

(30) Foreign Application Priority Data

Oct. 19, 2020 (JP) ................... 2020-175640

(51) Int. Cl.
G06T 7/00 (2017.01)
G06V 10/764 (2022.01)

(52) U.S. Cl.
CPC ............. *G06T 7/0012* (2013.01); *G06T 7/97* (2017.01); *G06V 10/764* (2022.01);
(Continued)

(58) Field of Classification Search
CPC ..... G06T 7/0012; G06T 7/97; G06T 2200/24; G06T 2207/10068; G06T 2207/20092;
(Continued)

(56) References Cited

U.S. PATENT DOCUMENTS

2009/0087049 A1 4/2009 Takahashi
2013/0152020 A1 6/2013 Nishiyama
(Continued)

FOREIGN PATENT DOCUMENTS

JP 2000-155788 A 6/2000
JP 2009-086765 A 4/2009
(Continued)

OTHER PUBLICATIONS

International Search Report issued in PCT/JP2021/033822; dated Nov. 9, 2021.
(Continued)

*Primary Examiner* — Robert J Michaud

(74) *Attorney, Agent, or Firm* — Studebaker & Brackett PC

(57) ABSTRACT

The medical image processing device includes a processor. The processor is configured to: acquire a plurality of medical images including a subject image; assign first image information to the medical image by analyzing the medical image; perform designation of the first image information; and perform control of displaying a selected image in a first display region of a display screen in a selected image display aspect, the selected image being the medical image to which the designated first image information is assigned among the plurality of medical images, and perform control of displaying each of pieces of designated first image information in a second display region of the display screen.

15 Claims, 16 Drawing Sheets

(52) U.S. Cl.
CPC ............... *G06T 2200/24* (2013.01); *G06T 2207/10068* (2013.01); *G06T 2207/20092* (2013.01); *G06T 2207/30096* (2013.01); *G06V 2201/034* (2022.01)

(58) Field of Classification Search
CPC ........ G06T 2207/30096; G06V 10/764; G06V 2201/034
See application file for complete search history.

(56) References Cited

U.S. PATENT DOCUMENTS

| | | | |
|---|---|---|---|
| 2017/0038951 A1* | 2/2017 | Reicher | G06F 16/583 |
| 2020/0134397 A1 | 4/2020 | Kim et al. | |
| 2020/0143538 A1 | 5/2020 | Kamon | |
| 2021/0042926 A1 | 2/2021 | Usuda | |

FOREIGN PATENT DOCUMENTS

| | | |
|---|---|---|
| JP | 2015-211862 A | 11/2015 |
| JP | 2020-081332 A | 6/2020 |
| WO | 2019/008942 A1 | 1/2019 |
| WO | 2019/220801 A1 | 11/2019 |

OTHER PUBLICATIONS

International Preliminary Report on Patentability (Chapter I) and Written Opinion of the International Searching Authority issued in PCT/JP2021/033822; dated Apr. 13, 2023.

The extended European search report issued by the European Patent Office on Feb. 28, 2024, which corresponds to European Patent Application No. 21882483.7-1126 and is related to U.S. Appl. No. 18/302,579.

* cited by examiner

FIG. 17

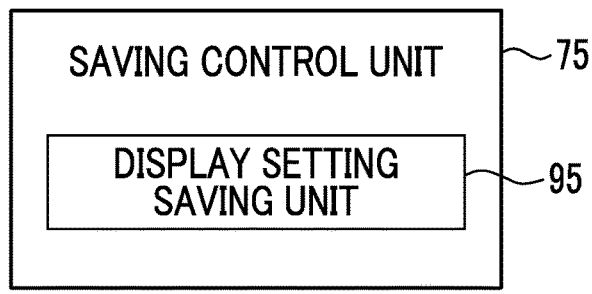

```
SAVING CONTROL UNIT               ~75
  ┌─────────────────────┐
  │ DISPLAY SETTING     │─95
  │ SAVING UNIT         │
  └─────────────────────┘
```

FIG. 18

| DISPLAY SETTING No.001 | SETTINGS FOR UPPER SCREENING | ~96 |
|---|---|---|
| USER No.: ×× AFFILIATION: ×× FACILITY No.: ×× | | |
| FIRST IMAGE INFORMATION DESIGNATION | SCHEMA, ESOPHAGOGASTRIC JUNCTION (Ae), DUODENAL DESCENDING LIMB, GREATER CURVATURE OF GASTRIC BODY, ANGULUS GASTRICI, CONVEXITY PART | |
| PRIORITY IMAGE | 1 LESION IMAGE<br>2 SAMPLE COLLECTION IMAGE<br>3 NORMAL IMAGE | |
| PRIORITY IMAGE | 1 LESION IMAGE<br>2 SAMPLE COLLECTION IMAGE<br>3 NORMAL IMAGE | |
| MAXIMUM NUMBER OF KEY IMAGES | TOTAL 10<br>3 IMAGES FOR EACH CATEGORY | |

MEDICAL IMAGE PROCESSING DEVICE, OPERATION METHOD OF MEDICAL IMAGE PROCESSING DEVICE, AND NON-TRANSITORY COMPUTER READABLE MEDIUM

CROSS-REFERENCE TO RELATED APPLICATIONS

This application is a Continuation of PCT International Application No. PCT/JP2021/033822 filed on 15 Sep. 2021, which claims priority under 35 U.S.C § 119(a) to Japanese Patent Application No. 2020-175640 filed on 19 Oct. 2020. The above application is hereby expressly incorporated by reference, in its entirety, into the present application.

BACKGROUND OF THE INVENTION

1. Field of the Invention

The present invention relates to a medical image processing device, an operation method of a medical image processing device, and a program for a medical image processing device.

2. Description of the Related Art

In a medical field, an image including a subject image acquired for examination, diagnosis, or the like (hereinafter, referred to as a medical image) is used. The acquired medical image is presented to a doctor. In addition, the doctor performs diagnosis and the like by using the medical image as one of determination materials. Specifically, the medical image includes an endoscope image, an X-ray image, a computed tomography (CT) image, a magnetic resonance (MR) image, and the like.

For example, in an examination using an endoscope system, after the examination is completed, an endoscopist needs to create a report in which an examination result, an opinion, and the like are described by using an endoscope image that is imaged by the endoscope system. However, in a case of the endoscope image to be attached to the report (hereinafter, referred to as a key image), there is a problem that it takes time and effort to select the endoscope image, such as a case where an endoscopist manually selects an endoscope image from a large number of endoscope images acquired in one examination.

For this reason, studies have been made on reducing a burden in selection of a key image. For example, there is known an information processing device that generates a key image from medical images obtained by imaging based on an analysis result of diagnosis information which is input (JP2015-211862A). In addition, there is known a medical report system that groups and displays medical images including a designated region-of-interest by designating a region-of-interest in the medical images (JP2009-86765A, corresponding to US2009/087049A1).

SUMMARY OF THE INVENTION

The criteria for selecting a key image are different for each medical facility or each user of the endoscope system, such an endoscopist, and are also different depending on the purpose of creation of a report. The report includes, for example, a report used when an endoscopist reports an examination result to a doctor who requests the examination and is in charge of a patient, a report for notifying a patient of an examination result, and the like. For this reason, even in a case where the key image is automatically selected, selection that is appropriate for each individual is not always performed.

In addition, the number of endoscope images acquired in one endoscopy may be enormous in some cases. In a case where key images are automatically selected from an enormous amount of endoscope images without limitation, the display may be difficult for a user to understand. For example, in a case where selected key images are displayed on a display while comparing selected endoscope images with non-selected endoscope images, a large number of endoscope images may be displayed.

An object of the present invention is to provide a medical image processing device, an operation method of a medical image processing device, and a non-transitory computer readable medium capable of easily and appropriately performing selection of a key image.

According to an aspect of the present invention, there is provided a medical image processing device including: a processor, in which the processor is configured to: acquire a plurality of medical images including a subject image; assign at least one of a plurality of pieces of first image information which are preset to the medical images by analyzing the medical images; perform designation of at least one of the plurality of pieces of first image information; and perform control of displaying a selected image in a first display region of an image display screen in a selected image display aspect, the selected image being the medical image to which the designated first image information is assigned among the plurality of medical images, and perform control of displaying each of the plurality of pieces of designated first image information in a second display region of the image display screen.

Preferably, the processor is configured to: assign at least one of a plurality of pieces of second image information which are preset to the medical images by analyzing the medical images; and set the selected image display aspect based on the second image information.

Preferably, each of the plurality of pieces of first image information which are preset is set in association with at least one of a plurality of categories, and the processor is configured to perform the designation for each of the categories.

Preferably, the processor is configured to: perform control of displaying the plurality of pieces of first image information in a third display region of the image display screen for each of the categories; and perform the designation based on a user's selection of the plurality of pieces of first image information displayed in the third display region.

Preferably, each of the plurality of pieces of second image information which are preset is set in association with at least one of a plurality of categories.

Preferably, the category is at least one of information on a part included in the subject image, information on an imaging condition of the medical image, information on a lesion included in the subject image, information on a region-of-interest included in the subject image, or information on a treatment tool included in the subject image.

Preferably, the processor is configured to: set a maximum number of the selected images to be displayed in the first display region; and perform control of displaying the selected images of which the number is equal to or smaller than the set maximum number in the first display region.

Preferably, the processor is configured to perform the analysis based on first correspondence information in which the medical image including the first image information and the first image information are associated with each other in advance.

Preferably, the processor is configured to perform the analysis based on second correspondence information in which the medical image including the second image information and the second image information are associated with each other in advance.

Preferably, designation performed by the processor is saved as a display setting, and the selected images are displayed on the image display screen based on the display setting.

Preferably, the display setting is saved for each of users.

Preferably, the display setting is saved for each user group including a plurality of users.

Preferably, the display setting is saved for each purpose of the imaging.

According to another aspect of the present invention, there is provided an operation method of a medical image processing device, the method including: an image acquisition step of acquiring a plurality of medical images obtained by imaging; an image information assignment step of assigning at least one of a plurality of pieces of first image information which are preset to the medical images by analyzing the medical images; a first image information designation step of performing designation of at least one of the plurality of pieces of first image information; and a display control step of performing control of displaying a selected image in a first display region of an image display screen in a selected image display aspect, the selected image being the medical image to which the designated first image information is assigned among the plurality of medical images, and performing control of displaying each of the plurality of pieces of designated first image information in a second display region of the image display screen.

According to still another aspect of the present invention, there is provided a non-transitory computer readable medium for storing a computer-executable program for causing a computer to function as a medical image processing device, the program causing the computer to execute: an image acquisition function of acquiring a plurality of medical images obtained by imaging; an image information assignment function of assigning at least one of a plurality of pieces of first image information which are preset to the medical images by analyzing the medical images; a first image information designation function of performing designation of at least one of the plurality of pieces of first image information; and a display control function of performing control of displaying a selected image in a first display region of an image display screen in a selected image display aspect, the selected image being the medical image to which the designated first image information is assigned among the plurality of medical images, and performing control of displaying each of the plurality of pieces of designated first image information in a second display region of the image display screen.

According to the present invention, it is possible to easily and appropriately perform selection of a key image.

BRIEF DESCRIPTION OF THE DRAWINGS

FIG. 4 is a block diagram illustrating an electrical configuration of a computer used in an endoscope image viewing support server or the like.

FIG. 17 is a block diagram illustrating an outline of functions of a saving control unit.

FIG. 18 is an explanatory diagram illustrating an example of a display setting.

DESCRIPTION OF THE PREFERRED EMBODIMENTS

In the present embodiment, an endoscope image is used as an example of a medical image. The endoscope image is an example of a medical image.

Figure 1:
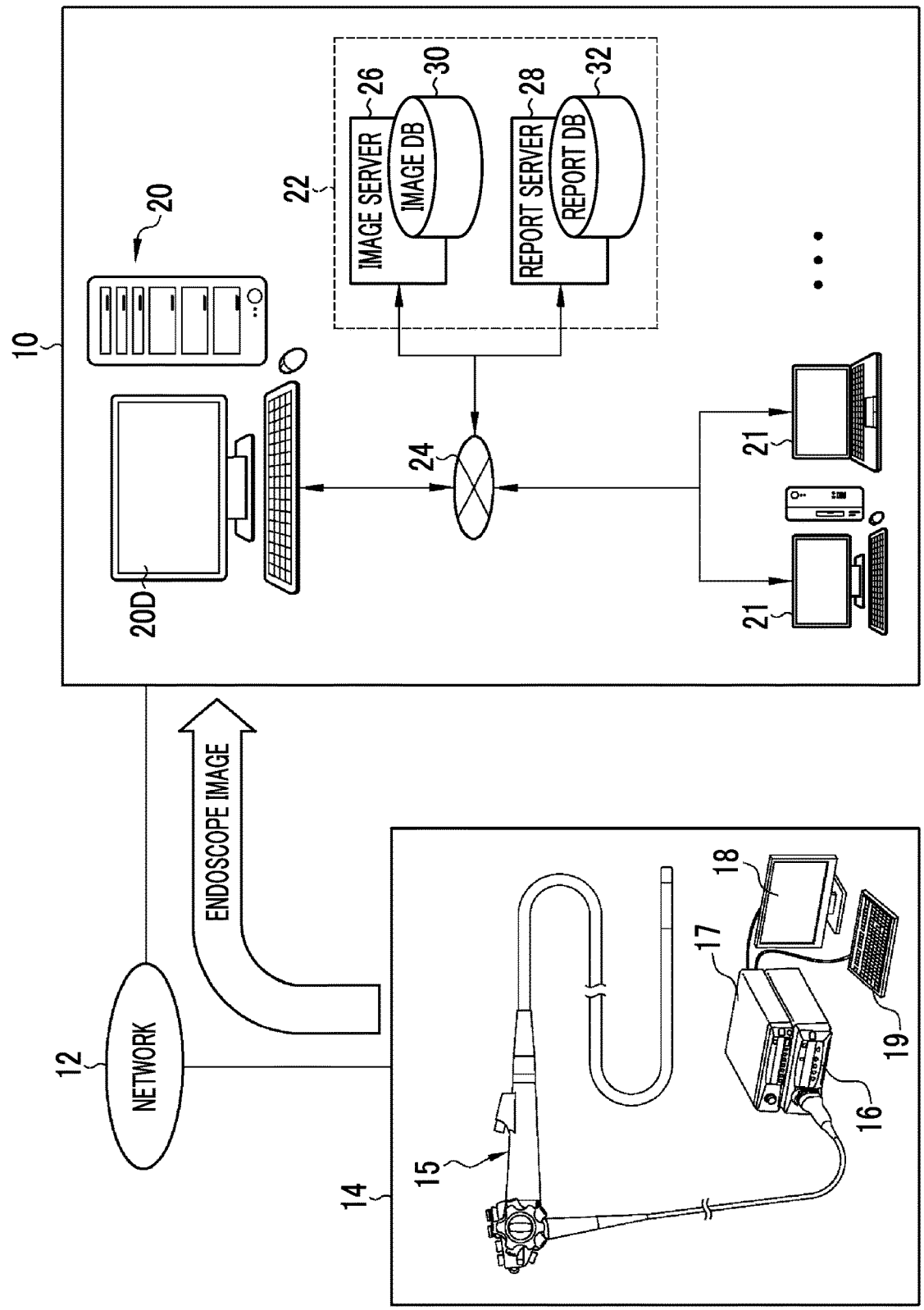
FIG. 1 is an explanatory diagram illustrating a schematic configuration of an endoscope image viewing support system.

An endoscope image viewing support system 10 illustrated in FIG. 1 is a computer system used to support viewing of an endoscope image 100 (refer to FIG. 2) obtained in an endoscopy, and is connected to an endoscope system 14 via a network 12. The network 12 is, for example, a local area network (LAN) in a hospital. The endoscope system 14 includes an endoscope 15, a light source device 16, a processor device 17, a display 18, and a keyboard 19 which is an input device.

The endoscope system 14 is used for an endoscopy (including various treatments using the endoscope 15). The endoscopy is performed by, for example, an endoscopist who has received a request from a doctor in charge of a patient, and a plurality of endoscope images 100 are obtained by performing the endoscopy. The endoscope image 100 imaged by the endoscope system 14 is saved in the endoscope image viewing support system 10.

The endoscope image viewing support system 10 includes an endoscope image viewing support server 20, a client terminal 21, and a server group 22, which are connected to each other via a network 24 such as a LAN.

The endoscope image viewing support server 20 is a medical image processing device according to the present invention, supports a user to select a key image from the plurality of endoscope images 100, and creates an examination report 34 (refer to FIG. 3) using the selected key image. The examination report 34 is a report obtained by viewing the endoscope image 100 and summarizing a medical opinion and the like by a doctor such as an endoscopist who performs an endoscopy. The endoscope image 100, which is a key image and is a basis for the opinion, is attached to the examination report 34. The examination report 34 is provided for viewing by a doctor in charge of a patient on whom an endoscopy is performed and is used for diagnosing the patient.

The server group 22 includes an image server 26 and a report server 28. The image server 26 includes an image database (hereinafter, referred to as an image DB) 30. The endoscope image 100 transmitted from the endoscope system 14 is stored in the image DB 30. The report server 28 includes a report database (hereinafter, referred to as a report DB) 32. The report DB 32 stores the examination report 34 created in accordance with an execution of the endoscopy. The image DB 30 and the report DB 32 are databases that can be searched by, for example, a patient identification data (ID) assigned to each patient, an examination ID assigned to each endoscopy, or the like.

The client terminal 21 is a terminal for viewing the endoscope image 100 and the examination report 34, and is used in a case where the endoscopist views the endoscope image 100 or creates the examination report 34 after the examination is completed. In addition, the client terminal 21 is used in a case where a doctor who is in charge of the patient views the endoscope image 100 or the examination report 34, the doctor being a doctor in a medical department who requests an endoscopy.

The client terminal 21 is, for example, a laptop computer or a desktop personal computer. In a case of creating an examination report 34 after an examination is completed, an endoscopist accesses the endoscope image viewing support server 20 by using the client terminal 21. In addition, the saved endoscope image 100 or the stored examination report 34 is read, and is displayed on a display of the client terminal 21. In this state, necessary work is performed, and an examination report 34 is completed. The completed examination report 34 is saved in the report server 28 via the endo scope image viewing support server 20.

A plurality of image folders (not illustrated) are provided in the image DB 30. In a case where an endoscopy is performed once, one image folder corresponding to the endoscopy is created. In addition, the endoscope image 100 acquired in the corresponding endoscopy is stored in each image folder. As described above, in the endoscopy, in addition to imaging of a motion picture, imaging of a still image at a certain timing by a freeze switch of the endo scope, automatic imaging performed at predetermined time intervals, test imaging or the like is also performed. All the images obtained by the imaging are stored in the image folder 36 as the endoscope images 100.

Figure 2:
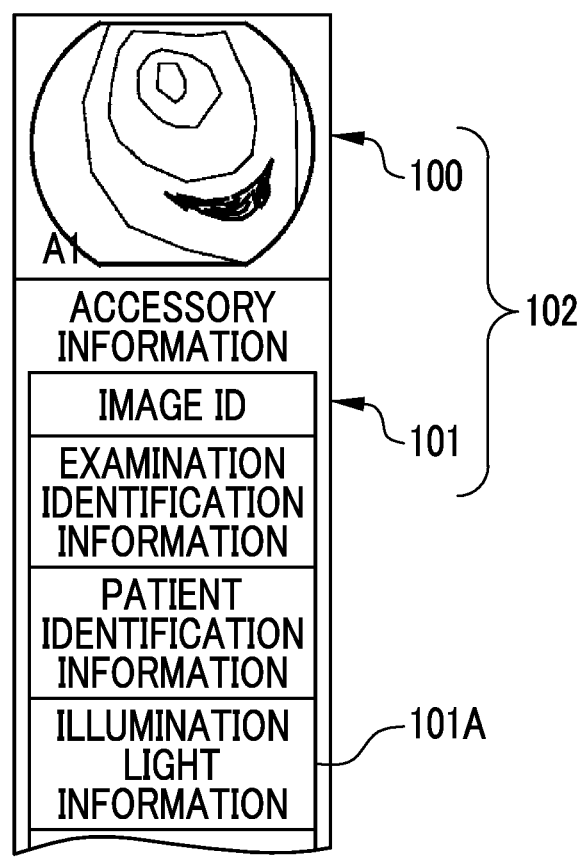
FIG. 2 is an explanatory diagram illustrating content of imaging information.

As illustrated in FIG. 2, these endoscope images 100 are stored in the image folders as imaging information 102 in which accessory information 101 such as a unique image ID, an imaging timing, and illumination light information 101A of the endoscope system 14 at the time of imaging are recorded in association with each other. In some cases, the accessory information 101 recorded with each endoscope image 100 is used as second image information to be described later for selecting a key image or for displaying and rearranging a key image on a display.

The image folder is created in a case where the endoscope image 100 which is transmitted from the endoscope system 14 and is in units of examination is saved in the image server 26. The image folder may be created in the endoscope system 14, and the image server 26 may receive each image folder. In addition, in a case where the image DB 30 stores the plurality of endoscope images 100 in a form that can be read in units of examination, such as tagging the endoscope images 100 in units of examination, the image folder may not be provided.

A plurality of report folders (not illustrated) are provided in the report DB 32. The examination report 34 created for each endoscopy is stored in the report folder. Similarly to the endoscope image 100, in a case where the examination report 34 is stored in the report DB 32 in a form that can be read for each endoscopy, such as tagging the examination report 34 in units of examination, the report folder may not be provided.

Figure 3:
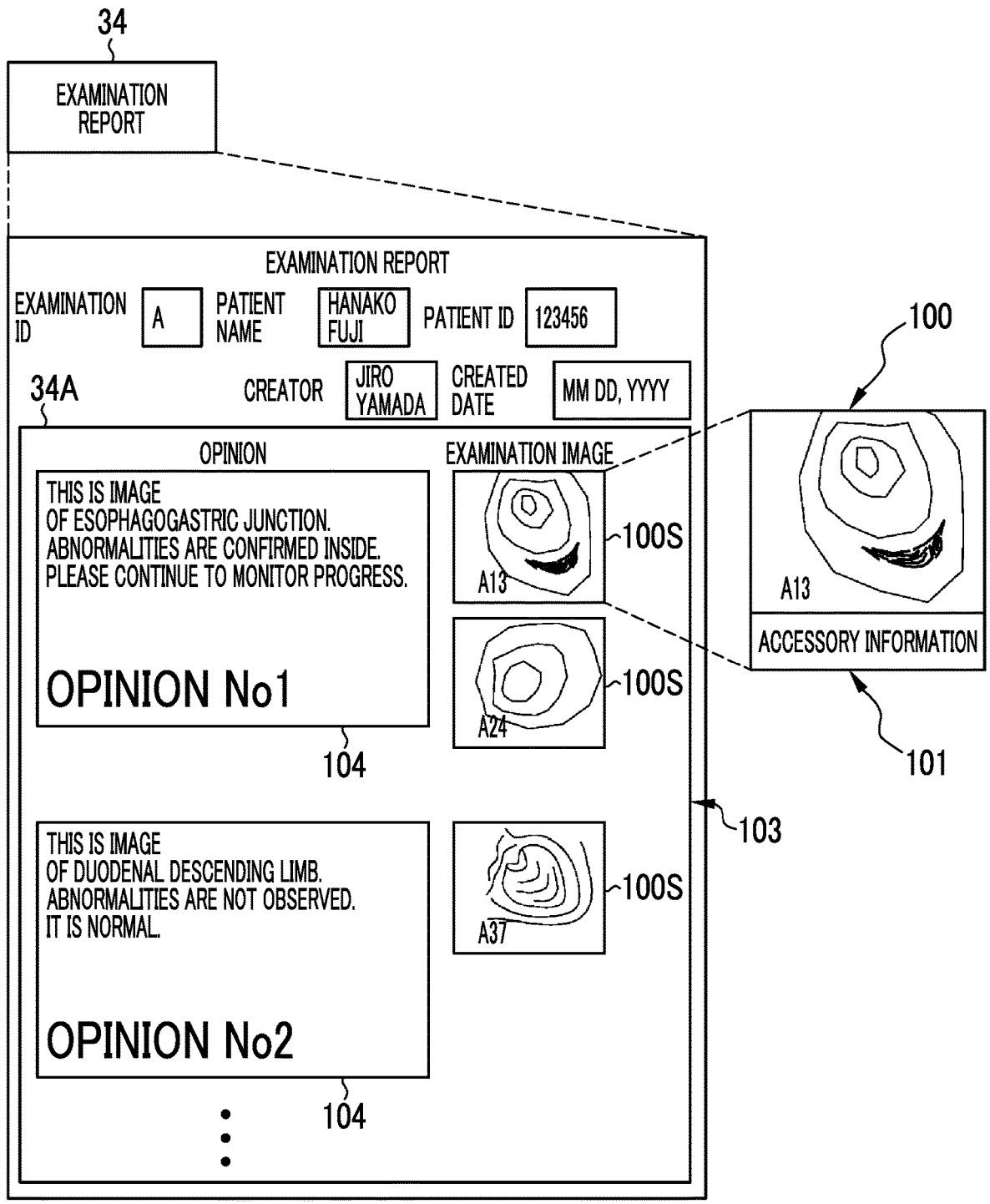
FIG. 3 is an explanatory diagram illustrating content of an examination report and a report display screen.

As illustrated in FIG. 3, the examination report 34 and a report display screen 103 in a case of displaying the examination report 34 include a report body 34A, examination identification information, patient identification information, and creator information indicating a creator. The report body 34A includes an opinion 104 of an endoscopist who performs the endoscopy and a key image 100S which is the endoscope image 100 attached to the examination report 34. The key image 100S is an endoscope image 100 that is a basis of the opinion 104, and is attached by being associated with each endoscopy. FIG. 3 illustrates an example in which two endoscope images 100 having image IDs A13 and A24 are associated with a first opinion 104 (opinion No1) and one endoscope image 100 having an image ID A37 is associated with a second opinion 104 (opinion No2).

In creation of the examination report 34, the endoscope image viewing support server 20 automatically selects an endoscope image 100 which is a key image based on a user's designation or the like from among the plurality of endoscope images 100 obtained in units of endoscopy, attaches the selected endoscope image 100 in accordance with the format of the examination report 34, and automatically lays out the examination identification information, the patient identification information, and the like obtained from the accessory information 101 associated with the endoscope image 100.

The endoscope image viewing support server 20, the client terminal 21, the image server 26 included in the server group 22, and the report server 28 are based on computers such as a personal computer, a server computer, or a workstation, and are configured by installing a control program such as an operating system and an application program such as a client program or a server program.

Figure 4:
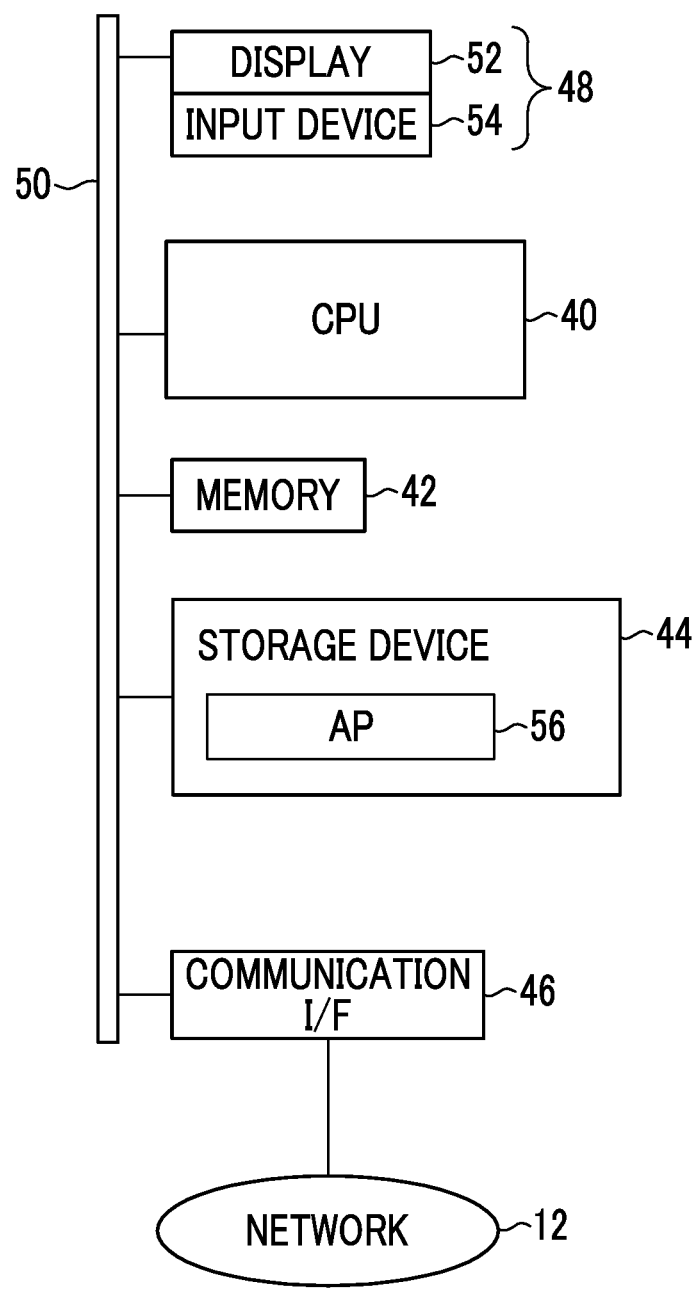

As illustrated in FIG. 4, the computers configuring the servers 20, 26, and 28 and the client terminal 21 have the same basic configuration, and each of the computers includes a central processing unit (CPU) 40, a memory 42, a storage device 44, a communication interface (I/F) 46, and an input/output unit 48. The components are connected to each other via a data bus 50. The input/output unit 48 includes a display 52 and an input device 54 such as a keyboard or a mouse.

The storage device 44 is, for example, a hard disk drive (HDD) or a solid state drive (SSD), and stores a control program or an application program (hereinafter, referred to as AP) 56. In addition, the server 26 and the server 28 in which the DB is configured are provided with, for example, a disk array in which a plurality of HDDs or the like are connected as a storage device 44 for the DB, in addition to the HDD or the like that stores the program. The disk array may be built in a server main body or may be provided separately from the server main body, and may be connected to the server main body via a network such as a LAN. In addition, as the storage device 44, a cloud storage connected via the Internet may be used.

The memory 42 is a work memory for the CPU 40 to execute processing, and is configured with a random access memory (RAM). The CPU 40 loads the control program stored in the storage device 44 into the memory 42, and collectively controls each unit of the computer by executing processing according to the program. The communication I/F 46 is a network interface that controls transmission to and from the network 12.

A client program is installed in the client terminal 21 as the AP 56. The client program is a program for causing the client terminal 21 to access the endoscope image viewing support server 20 and execute a function of transmitting various requests such as a viewing request or an update request of an image display screen such as a display image setting screen 105 (refer to FIG. 9) or a key image automatic selection screen 106 (refer to FIG. 11) for selecting a key image or a function of receiving and displaying the image display screen transmitted from the endoscope image viewing support server 20 to the client terminal 21. The client program may be exclusively programmed for the endoscope image viewing support system 10 or may include a well-known web browser.

Figure 5:
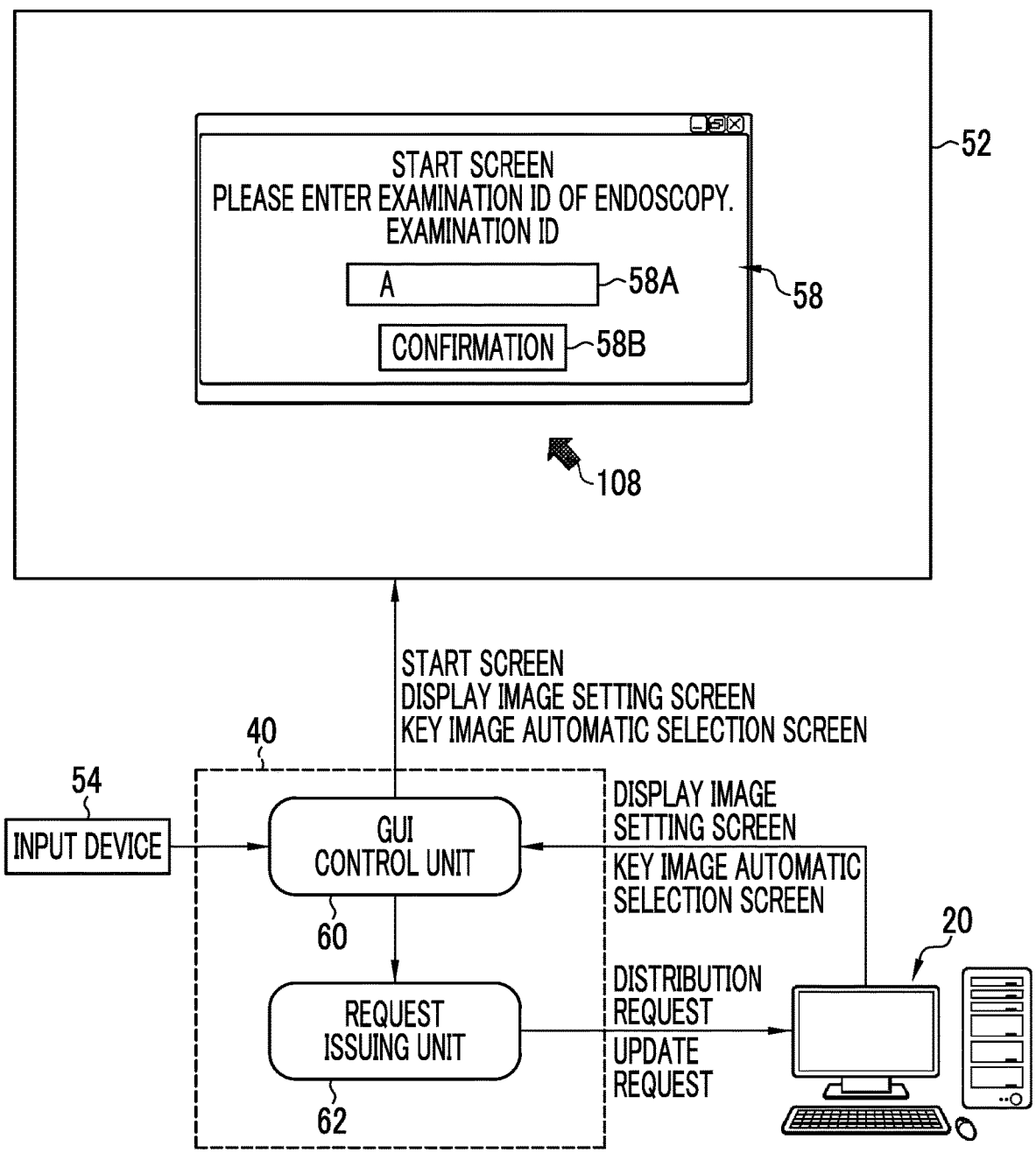
FIG. 5 is an explanatory diagram illustrating an outline of functions of a client terminal.

As illustrated in FIG. 5, in a case where the client program is started, a start screen 58 provided with an operation function by a graphical user interface (GUI) is displayed on the display 52 of the client terminal 21, and the CPU 40 of the client terminal 21 functions as a request issuing unit 62 that issues various requests to the GUI control unit 60 and the endoscope image viewing support server 20 in cooperation with the memory 42 and the like.

The start screen 58 is provided with an examination ID input field 58A and a confirmation button 58B. In a case where an examination ID is input in the examination ID input field 58A and the confirmation button 58B is operated, one endoscopy can be designated from a plurality of endoscopies. In a case where the endoscopy is designated, information which is input in the examination ID input field 58A is transmitted from the GUI control unit 60 to the request issuing unit 62. The request issuing unit 62 generates a distribution request of an image display screen for selecting the endoscope image 100 to be attached to the report among the endoscope images 100 corresponding to the designated endoscopy, that is, the endoscope images 100 of the endoscopy corresponding to the examination ID which is input in the examination ID input field 58A, and issues the distribution request to the endoscope image viewing support server 20. In response to the distribution request, the endoscope image viewing support server 20 distributes an image display screen in an initial state or with a setting which is saved in advance, and thus the image display screen is displayed on the display 52 of the client terminal 21.

The image display screen includes data described in, for example, a markup language such as an extensible markup language (XML), and the image display screen itself also has an operation function by GUI. The GUI control unit 60 receives an operation instruction from the input device 54 via the image display screen, such as an input operation from the keyboard or a click operation of an operation button according to a pointer 108 of the mouse. The request issuing unit 62 issues an update request of the image display screen or the like in response to the operation instruction received by the GUI control unit 60.

The update request includes an instruction to update display content of the image display screen, such as various instructions for selecting a key image via the image display screen and an instruction to switch the endoscope image 100 or the like to be displayed. In a case where the update request is transmitted to the endoscope image viewing support server 20, the endoscope image viewing support server 20 updates the image display screen and distributes the updated image display screen to the client terminal 21. Thereby, the image display screen displayed on the client terminal 21 is updated.

Figure 6:
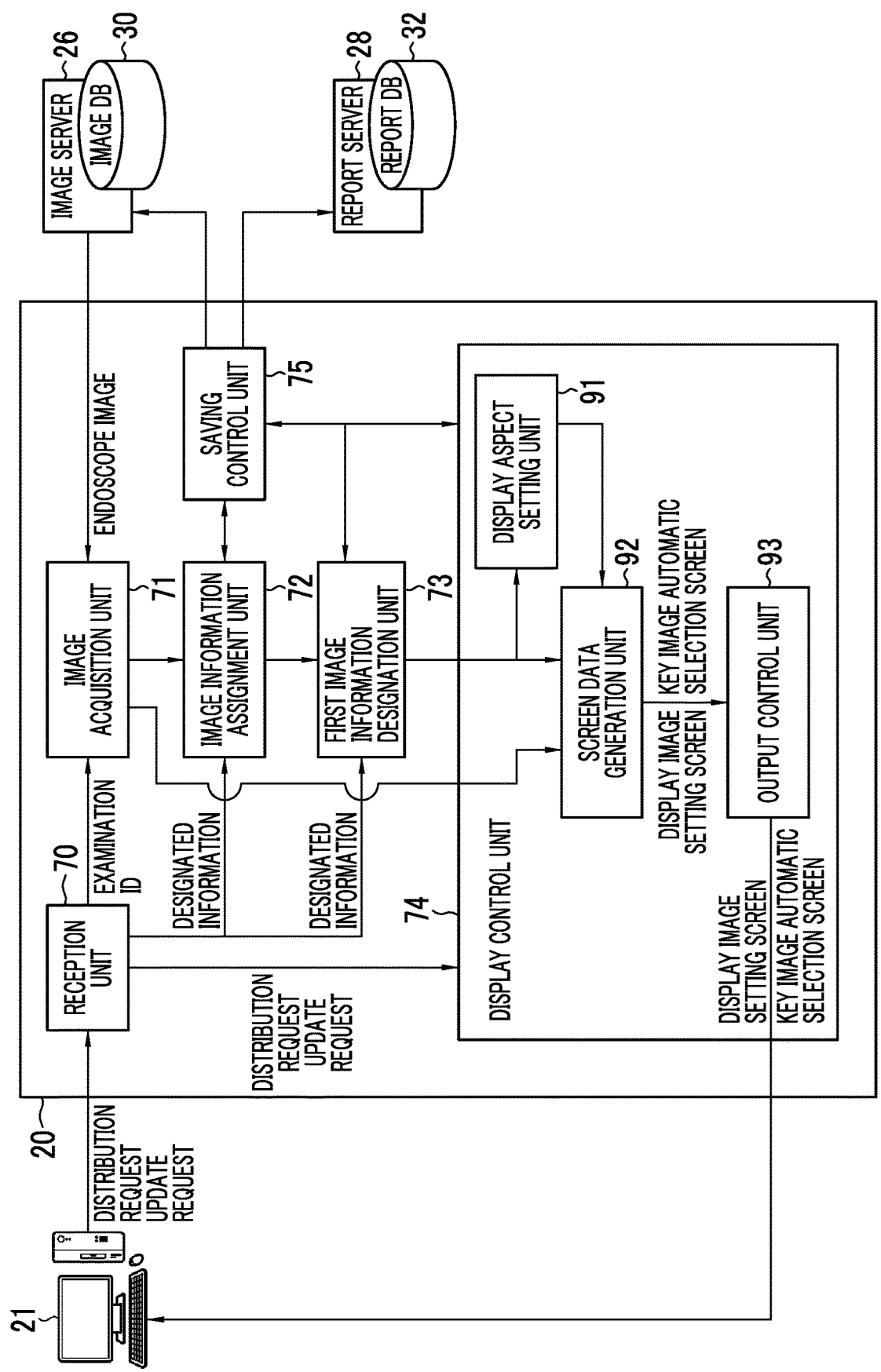
FIG. 6 is an explanatory diagram illustrating an outline of functions of the endoscope image viewing support server.

As illustrated in FIG. 6, the server program installed as the AP 56 in the endoscope image viewing support server 20 is an operation program for causing the computer to function as the endoscope image viewing support server 20. In a case where the server program is started, the CPU 40 of the endoscope image viewing support server 20 functions as a reception unit 70, an image acquisition unit 71, an image information assignment unit 72, a first image information designation unit 73, a display control unit 74, and a saving control unit 75 in cooperation with the memory 42 and the like.

The reception unit 70 receives inputs from various terminals. The reception unit 70 receives the distribution request or the update request of the image display screen that is input from the client terminal 21, and outputs the request to the display control unit 74. The distribution request of the image display screen is for requesting distribution of the image display screen that displays the endoscope image 100 selected from the plurality of endoscope images 100 designated by the examination ID which is input in the examination ID input field 58A of the start screen 58. In a case where the distribution request is received, the reception unit 70 inputs the examination ID designated in the distribution request (examination ID which is input in the examination ID input field 58A) to the image acquisition unit 71. The update request includes designation information or various settings, the designation information being information for designating at least one of a plurality of pieces of first image information to be described later and for designating at least one of a plurality of pieces of second image information to be described later. The designation information is input to the image information assignment unit 72 and the first image information designation unit 73.

In a case where the examination ID is input, the image acquisition unit 71 accesses the image server 26 and acquires, from the image DB 30, all the endoscope images 100 obtained by the endoscopy corresponding to the notified examination ID. Specifically, the image acquisition unit 71 searches for the image DB 30 by using the examination ID as a search keyword, and reads and acquires the imaging information 102 having the same examination ID from the image folder 36 of the image DB 30. As described above, the imaging information 102 includes the endoscope image 100 and the accessory information 101 recorded in association with the endoscope image 100. Thereby, the plurality of endoscope images 100 in units of examination that are obtained in one endoscopy and the accessory information 101 recorded in association with the endoscope images 100 are all acquired. The image acquisition unit 71 outputs the acquired imaging information 102 to the image information assignment unit 72.

The image information assignment unit 72 assigns, to the endoscope image 100, at least one of the plurality of pieces of first image information which are preset by analyzing the endoscope image 100. Specifically, assignment of the first image information to the endoscope image 100 is realized by adding the first image information to the accessory information 101 included in the imaging information 102, or by adding information indicating that the first image information is included in a case where the first image information is already present in information included in the accessory information 101. Therefore, adding information indicating the first image information to any piece of information included in the accessory information 101 in advance is also included in the analysis of the endoscope image 100. A plurality of pieces of first image information may be assigned.

Figure 7:
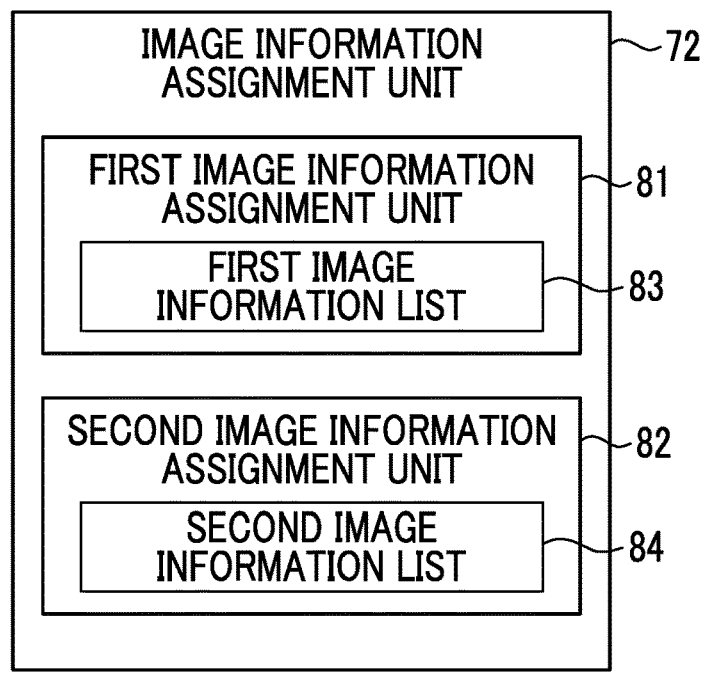
FIG. 7 is a block diagram illustrating an outline of functions of an image information assignment unit.

As illustrated in FIG. 7, the image information assignment unit 72 includes a first image information assignment unit 81 and a second image information assignment unit 82. The first image information assignment unit 81 includes a first image information list 83, and the second image information assignment unit 82 includes a second image information list 84. The second image information will be described later.

The first image information list 83 is a list in which a plurality of pieces of first image information are described, and is preset. Preferably, each of the plurality of pieces of first image information is set in association with at least one of a plurality of categories. Therefore, in the first image information list 83, each of the plurality of pieces of first image information is described in association with at least one of the plurality of categories.

One of the plurality of categories is, for example, information on a part included in a subject image. In a case where a category of a part is set, specific item names included in the category of the part, for example, part names such as "esophagus", "esophagogastric junction", "greater curvature of gastric body", "vestibular part", "angulus gastrici", "convexity part", and "duodenal descending limb" are preset as the first image information.

In addition, examples of other categories include information on an imaging condition of the medical image, information on a lesion included in the subject image, information on a region-of-interest included in the subject image, information on a treatment tool included in the subject image, and the like.

The information on the imaging condition is information on imaging when the medical image is acquired. In a case where a category of the imaging condition is set, for example, a type of illumination light, a distance between a subject and a tip portion of the endoscope, an exposure, or a type of the endoscope used are set as the first image information. In a case where the information on the lesion included in the subject image is set as a category, for example, whether or not the subject image includes the lesion, a size of the lesion, a type of the lesion, and the like are set as the first image information. In a case where the information on the region-of-interest included in the subject image is set as a category, whether or not the subject image includes the region-of-interest, a size of the region-of-interest, biological information such as an oxygen saturation of the region-of-interest, and the like are set as first image information. In a case where the information on the treatment tool included in the subject image is set as a category, whether or not the subject image includes the treatment tool, a type of the treatment tool, whether or not the image is a sample collection image, and the like are set as the first image information. In a case where the first image information is the information on the treatment tool, the first image information can be set as the "sample collection image".

This is because it is possible to analyze whether or not the image is a sample collection scene based on the type of the treatment tool included in the subject image. The first image information is saved in advance in the first image information list 83, and is used.

The first image information assignment unit 81 assigns, to the endoscope image 100, at least one of the plurality of pieces of first image information which are preset by analyzing the endoscope image 100 using image processing. The plurality of pieces of first image information which are preset are pieces of the first image information included in the first image information list 83. In addition, preferably, the first image information assignment unit 81 analyzes the endoscope image 100 for each category included in the first image information list 83. For example, in a case where the first image information list 83 includes a category of information on a part included in the subject image, the first image information assignment unit 81 analyzes the endoscope image 100 in relation to the category of the part, and assigns, to the endoscope image 100, the first image information included in the category of the part. In addition, in a case where the first image information list 83 includes a plurality of categories, the endoscope image 100 is analyzed for each category, or the endoscope image 100 is analyzed in relation to the first image information included in the plurality of categories.

The first image information assignment unit 81 assigns the first image information to the endoscope image 100 by writing the first image information in the accessory information 101 of the endoscope image 100. In a case where the first image information which is preset cannot be assigned to the endoscope image 100 for some reason, "unknown" is assigned as the first image information such that the user or the like can recognize the fact. Therefore, "unknown" or the like is written in a column of the first image information of the accessory information 101 of the endoscope image 100.

For the analysis of the endoscope image 100 by image processing, various image processing methods for determining or recognizing the first image information can be adopted. In the various image processing methods, it is preferable to use a method of preparing an endoscope image that is determined as including the first image information and performing analysis based on correspondence information in which the endoscope image and the first image information are associated with each other in advance. Preferably, the correspondence information is a model trained by a machine learning technique. Therefore, for example, in a case where the category of the first image information is a part, analysis is performed on the endoscope image 100 in which the part included in the subject image is unknown by using a trained model obtained by performing learning using learning data a plurality of times, the learning data being data in which an endoscope image obtained by imaging a specific part as a subject and a part name, for example, "esophagus" are associated with each other. Thereby, the part name included in the subject image is obtained as an analysis result. Specifically, in a case where a part appearing in the endoscope image 100, that is, a part included in the subject image is an "esophagus", analysis is performed by using the trained model, and thus an analysis result of "esophagus" can be obtained as the first image information.

The first image information designation unit 73 designates at least one of the plurality of pieces of first image information. By designating the first image information, in the plurality of endoscope images 100, the imaging information 102 which includes the designated first image information in the accessory information 101 and the imaging information 102 which does not include the designated first image information in the accessory information 101 can be classified. For example, the plurality of pieces of first image information are a plurality of specific part names in a case where the first image information is a category of a part. Therefore, for example, by designating a part name to be attached to the examination report 34 from the plurality of part names, the endoscope image 100 which includes the part name in the imaging information 102 can be extracted.

As described above, the designation of the first image information is performed, for example, by selection of the first image information that is input via the display image setting screen 105 or the like from the client terminal 21 by the user. Specifically, in a case where the first image information is a part name, the user selects the first image information by inputting at least one of part names which are pieces of the first image information, such as "esophagus", to the client terminal 21. The input information is received as designated information by the first image information designation unit 73, and the first image information designation unit 73 classifies the imaging information 102 which includes the first image information of "esophagus" and other the imaging information 102 which does not include the first image information of "esophagus". In addition, in the accessory information 101 of the endoscope image 100 including the first image information of "esophagus", it is written that the designated first image information is assigned to the endoscope image 100.

The display control unit 74 includes a display aspect setting unit 91, a screen data generation unit 92, and an output control unit 93. The endoscope image 100 is directly input to the screen data generation unit 92 from the image acquisition unit 71.

In addition, the display control unit 74 sets, as a selected image, the endoscope image 100 to which the designated first image information is assigned among the plurality of endoscope images 100 which are input via the first image information designation unit 73. In addition, the display control unit 74 performs control of displaying the selected image in a first display region of the image display screen in a selected image display aspect based on a setting of the display aspect setting unit 91. In addition, the display control unit 74 performs control of displaying each of the pieces of designated first image information in a second display region of the image display screen. The selected image display aspect can be preset. In addition, the selected image display aspect may be set by the display aspect setting unit 91 based on the second image information to be described later.

The image display screen includes the first display region and the second display region, and the selected image is controlled to be displayed in the first display region in the selected image display aspect. In addition, each of the plurality of pieces of first image information is controlled to be displayed in the second display region. The selected image and each of the plurality of pieces of first image information are displayed in, for example, a key image automatic selection screen 106. The key image automatic selection screen 106 corresponds to the image display screen. Therefore, the first display region and the second display region can be display regions in the key image automatic selection screen 106. For example, the key image automatic selection screen 106 is divided into two regions, one region is used as the first display region, and the other region is the second display region. The key image automatic selection screen 106 is displayed on the display 52.

The selected image is controlled to be displayed in the first display region of the key image automatic selection screen 106 in the selected image display aspect. The selected image display aspect includes an aspect of a position at which the selected image is displayed in the first display region and/or an aspect of a display method for emphasizing and displaying a specific selected image as compared with other selected images. In the aspect of the position, one or a plurality of selected images are provided. In a case where a plurality of selected images are provided, an area of the first display region is limited. For this reason, a selected image to be displayed is further selected. Alternatively, a priority is assigned to a selected image to be displayed, and a display position of the selected image is controlled and displayed. The selected image display aspect can be preset. Examples of the aspect of the display method include various highlight displays and the like.

Each of the pieces of designated first image information is controlled to be displayed in the second display region of the image display screen. For example, in a case where the first image information is a category of a part, all the part names of the pieces of designated first image information are displayed in the second display region. Thereby, it is possible to recognize the first image information corresponding to the selected key image at a glance. Therefore, in a case where an examination report 34 to which a desired endoscope image 100 is attached is to be created, in order to adjust the insufficient endoscope image 100 or the excessive endoscope image 100, it is also possible to immediately recognize how to designate the first image information.

The screen data generation unit 92 generates and updates a key image automatic selection screen 106 that displays the endoscope image 100 or each of the pieces of the designated first image information based on the selected image display aspect which is set, the endoscope image 100 being the selected image which is input to the screen data generation unit 92. The screen data generation unit 92 appropriately uses the imaging information 102 including the endoscope image 100 and the accessory information 101, the first image information, and the like, according to the screen requested by the client terminal 21. In a case of generating and updating the key image automatic selection screen 106, the screen data generation unit 92 creates a key image automatic selection screen 106 by using the selected image display aspect, or the endo scope image 100 which is the selected image and the accessory information 101 recorded in association with the endoscope images 100.

The generated and updated key image automatic selection screen 106 is input to the output control unit 93. The output control unit 93 distributes the key image automatic selection screen 106 which is input, to the client terminal 21 as a request source. In the client terminal 21, the key image automatic selection screen 106 distributed from the output control unit 93 is displayed on the display 52. The user can recognize whether or not the endoscope image 100 to be attached to the examination report 34 is excessive or insufficient by the key image automatic selection screen 106 displayed on the display 52.

Figure 8:
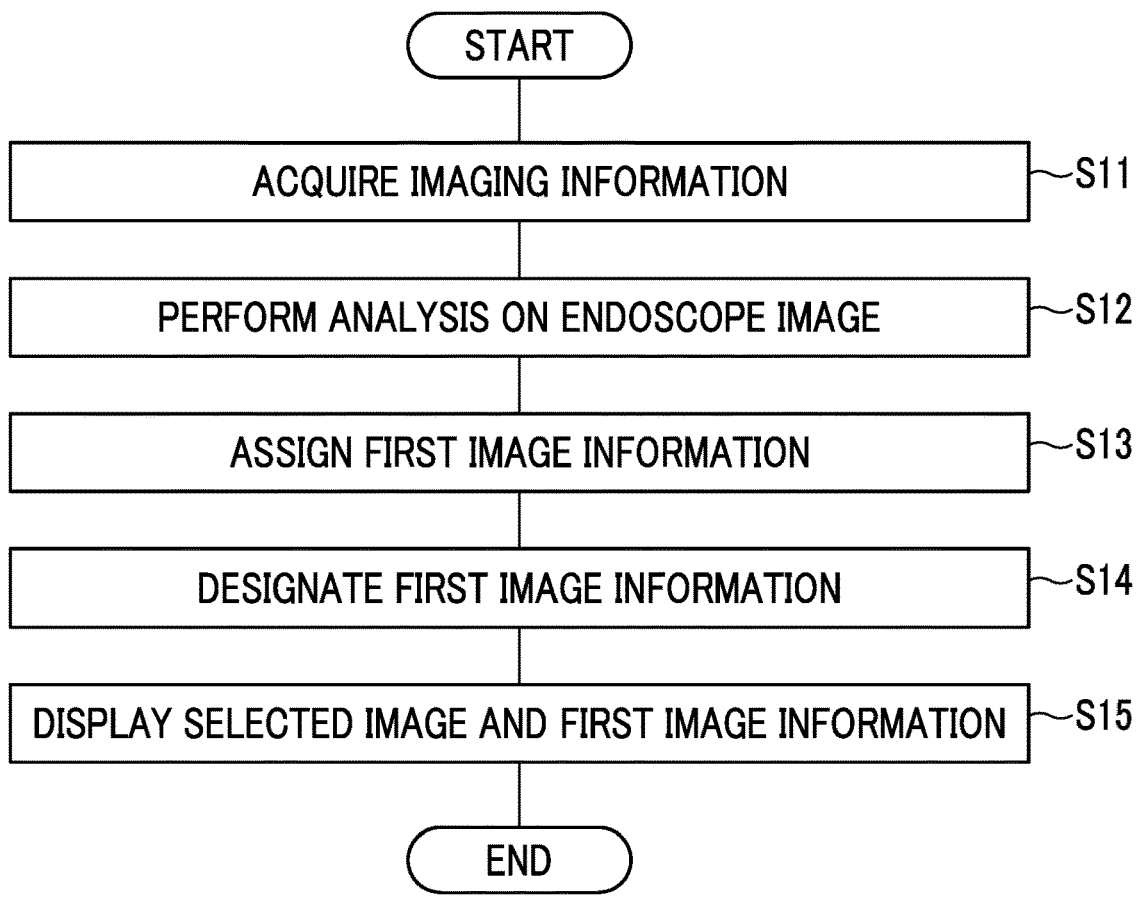
FIG. 8 is a flowchart illustrating a processing procedure of key image automatic selection.

A flow of the key image automatic selection, specifically, acquisition of the endoscope image 100 in the endoscope image viewing support server 20, assignment of the first image information, designation of the first image information, and display of the selected image and the first image information on the display will be described with reference to a flowchart illustrated in FIG. 8 and explanatory diagrams illustrated in FIG. 9 to FIG. 14.

In the present embodiment, in the key image automatic selection, the display screens of the display image setting screen 105 (refer to FIG. 9) and the key image automatic selection screen 106 (refer to FIG. 10) are displayed on the display 52. The display image setting screen 105 is a screen for setting an endoscope image or the like to be displayed on the key image automatic selection screen 106, and the display image setting screen 105 and the key image automatic selection screen 106 have the same layout.

First, in a case where a distribution request from the client terminal 21 is received as described above, the image acquisition unit 71 searches for the image DB 30, and reads and acquires pieces of imaging information 102 in units of examination that are obtained in one endoscopy, that is, a plurality of endoscope images 100 and pieces of accessory information 101 recorded in association with the endoscope images 100 from the image DB 30 (S11).

Next, the image information assignment unit 72 performs analysis on each of the plurality of endoscope images 100 which are acquired in units of examination in relation to the first image information (S12). As described above, the first image information can be selected from a plurality of categories, and is preset by a user's selection or the like.

Figure 9:
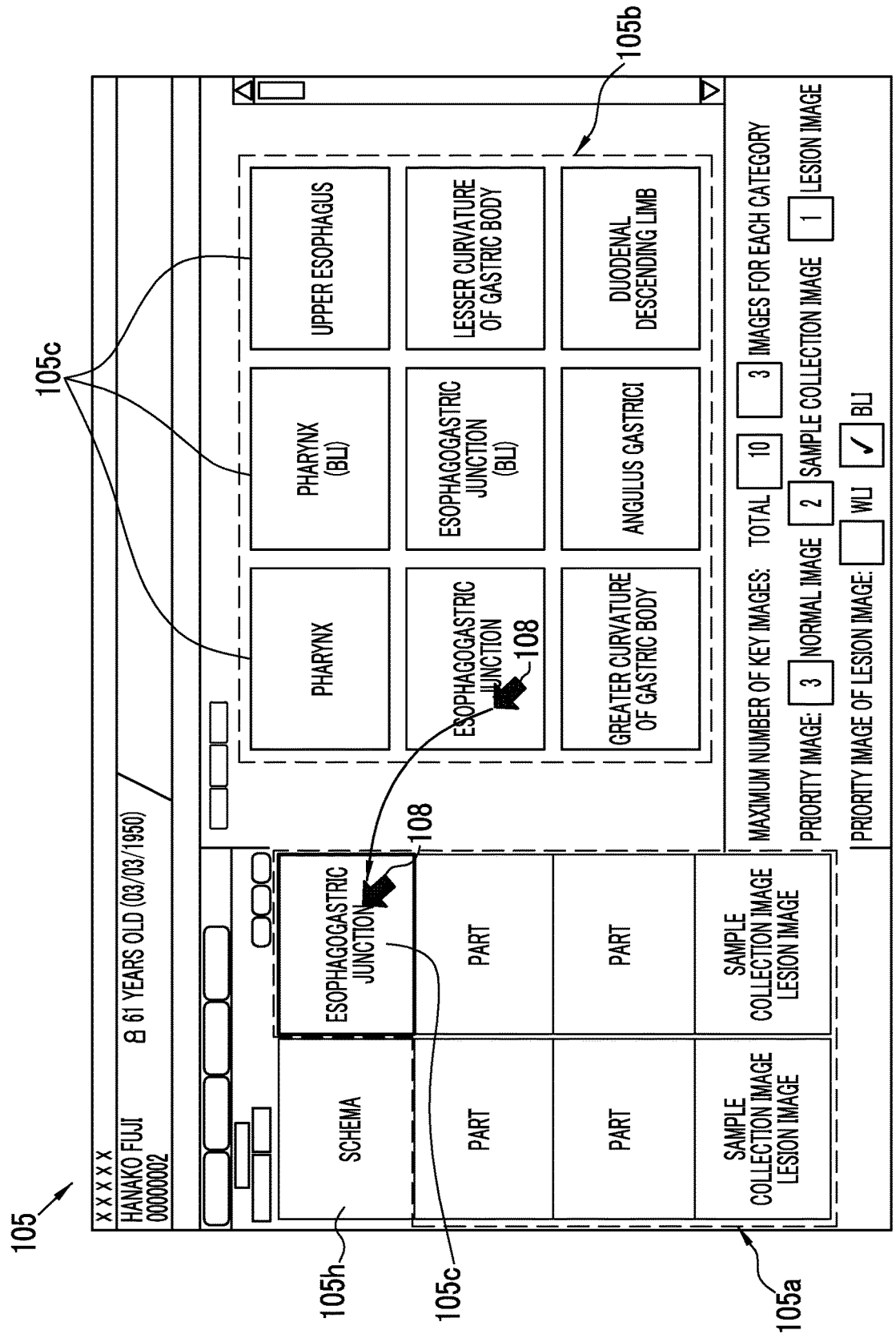
FIG. 9 is an image diagram illustrating a display image setting screen in which a first image information block is moved.

As illustrated in FIG. 9, the user presets the first image information by using the display image setting screen 105. The display image setting screen 105 includes a category setting button (not illustrated). The user sets at least one of the categories by operating the category setting button. In the present embodiment, a category of a part is set. In the category of the part, a plurality of part names are preset as the first image information. Therefore, in a case where the category of the part is selected, the plurality of part names are set as the first image information, and the image information assignment unit 72 performs analysis on the endoscope image 100. Thereby, a part name which is the first image information is obtained as an analysis result.

In this way, the plurality of pieces of first image information which are preset are displayed in a non-selection region 105b of the display image setting screen 105, which is one of the display screens, for each category. The non-selection region 105b corresponds to a third display region.

A plurality of first image information blocks 105c indicating the part names included in the category of the part are displayed in the non-selection region 105b. One first image information block 105c indicates one piece of the first image information. Since the first image information block 105c is for displaying the first image information, in the present embodiment, the part name is displayed. On the other hand, in a case where a category other than a part is set, the first image information included in the set category is displayed.

By the analysis of the endoscope image 100 by the image information assignment unit 72, the first image information of the set category is assigned to the endoscope image 100 (S13). In the present embodiment, since the category of the part is set, the image information assignment unit 72 assigns the part name described in the first image information block 105c to each of the endoscope images 100 by analyzing each of the plurality of acquired endoscope images 100. In the drawings, the reference numeral may be attached only to a portion in order to avoid complication of the drawings.

At least one of the plurality of pieces of first image information which are sets as described above is designated (S14). The designation is performed by the user. On the other hand, in some cases, the designation is performed by a person other than the user, such as the same designation as in the previous time. In this way, it is preferable to designate the first image information based on the user's selection of the plurality of pieces of first image information displayed in the non-selection region 105b. In the present embodiment, the first image information is designated by using the first image information blocks 105c which indicate the part names and are displayed in the non-selection region 105b of the display image setting screen 105.

In a case where the user designates the first image information, the first image information block 105c of the non-selection region 105b is designated and dragged by a pointer 108. Thereby, the first image information block 105c is moved to be included in the selection region 105a. The first image information block 105c included in the selection region 105a is the first image information designated by the user. In the selection region 105a, the designated first image information is highlighted and displayed. In the embodiment illustrated in FIG. 9, the first image information of "esophagogastric junction" is one of a plurality of pieces of designated first image information. The user designates the plurality of pieces of first image information by repeating such an operation.

Figure 10:
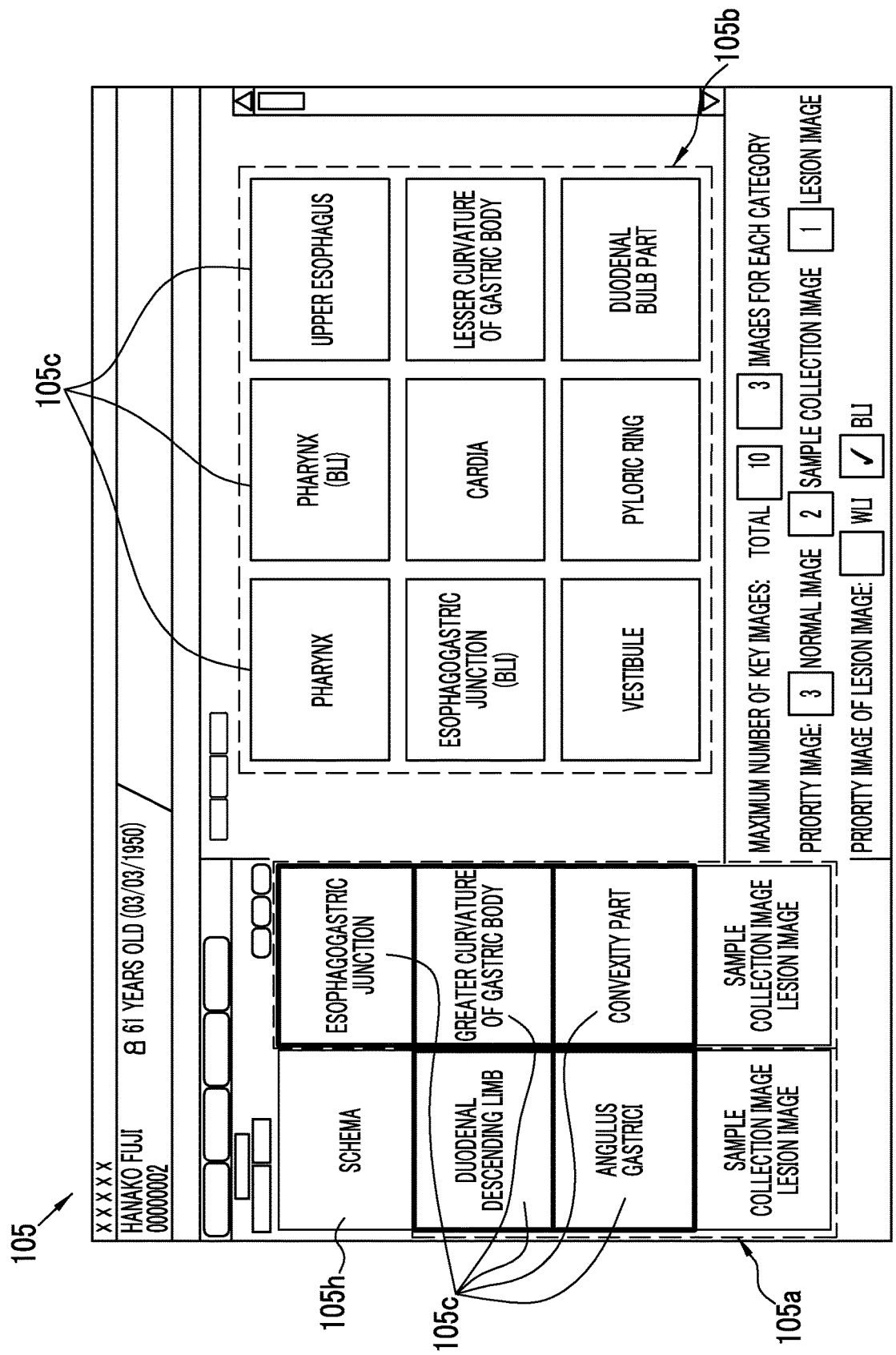
FIG. 10 is an image diagram illustrating a display image setting screen in which a plurality of first image information blocks are moved.

As illustrated in FIG. 10, as a result of the designation by the user, on the display image setting screen 105, the selection region 105a includes five types of the first image information blocks 105c, and pieces of the first image information designated by the user are five types of part names.

As described above, the first image information is designated. In FIG. 10, the first image information block 105c that is not designated is displayed in the non-selection region 105b. The first image information designation unit 73 designates the first image information based on the designation of the user. Therefore, the first image information designation unit 73 sets, as the designated first image information, the part name indicated by the first image information block 105c that is moved to the selection region 105a. Since a part name is assigned to each of the plurality of acquired endoscope images 100 by the image information assignment unit 72, the endoscope image 100 having the part name that is the designated first image information is selected from the plurality of acquired endoscope images 100, and the selected endoscope image 100 is set as a selected image. In this way, preferably, the first image information designation unit 73 designates the first image information based on the plurality of pieces of first image information displayed in the selection region 105a.

Figure 11:
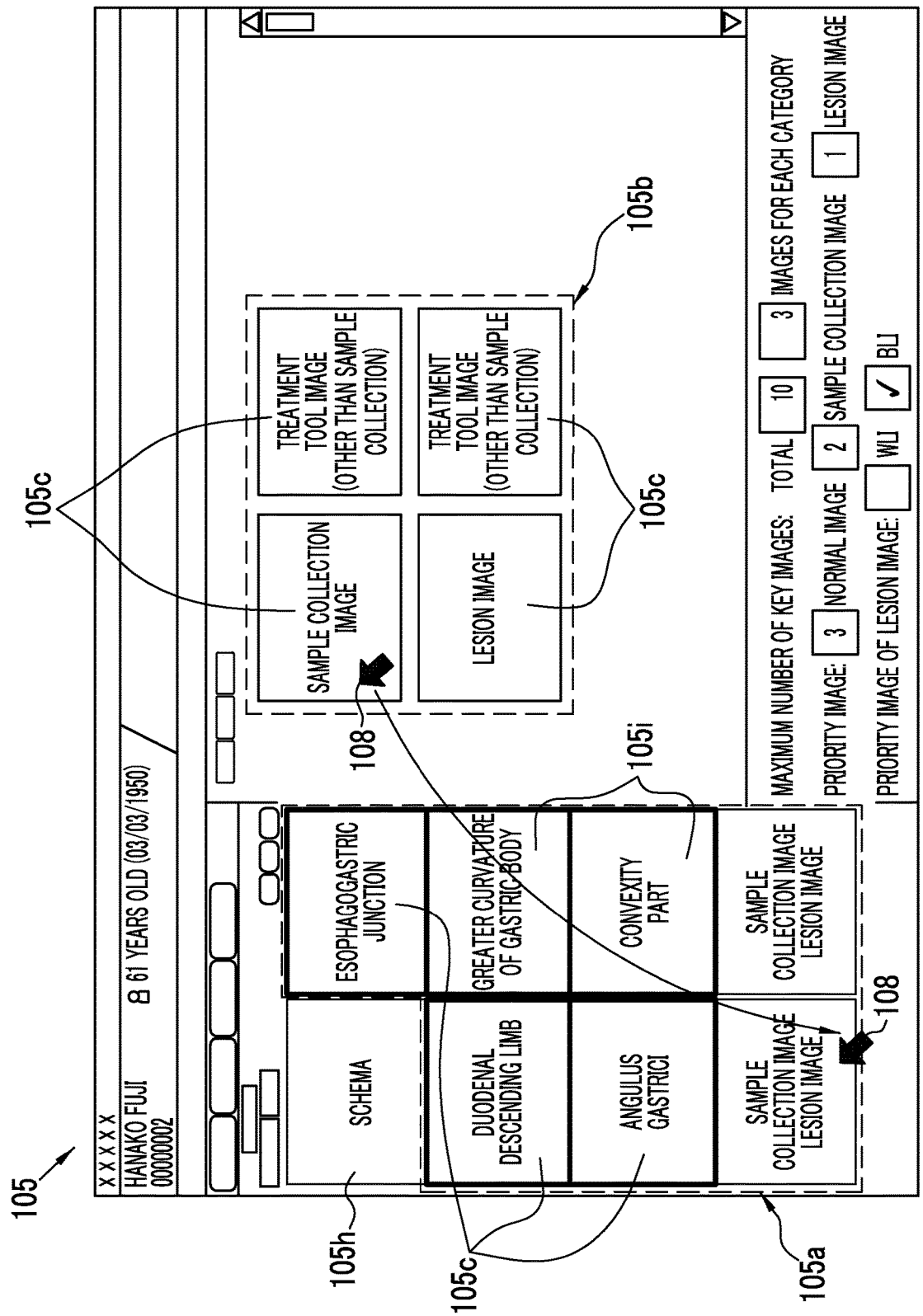
FIG. 11 is an image diagram illustrating a display image setting screen in which a first image information block of another category is moved.

Here, by switching the category of the first image information, it is possible to designate the first image information included in a category other than the category of the part. As illustrated in FIG. 11, on the display image setting screen 105, the category is switched to the category of the information on the treatment tool by the category setting button (not illustrated) in the same manner as in the case of the category of the part.

In the non-selection region 105b, two first image information blocks 105c, which are "sample collection image" and "non-sample collection image", are displayed as the category of the information on the treatment tool included in the subject image. In addition, two first image information blocks 105c, which are "lesion image" and "non-lesion image", are displayed as the category of information on the lesion included in the subject image. In this way, the first image information blocks 105c of the plurality of categories may be controlled to be displayed in the non-selection region 105b according to the area of the display region or the like. Similar to the case of the category of the part described above, the user designates the first image information of each category by moving the first image information block 105c from the non-selection region 105b to the selection region 105a.

In the present embodiment, "sample collection image" is designated as the first image information from the category of the information on the treatment tool, and "lesion image" is designated as the first image information from the category of the information on the lesion. Similar to the case of the category of the information on the part, the image information assignment unit 72 performs analysis for assigning the first image information of "sample collection image" to the endoscope image 100 including a scene in which a sample is being collected in the subject image. In addition, the image information assignment unit 72 performs analysis for assigning the first image information of "lesion image" to the endoscope image 100 including a lesion in the subject image. The analysis method can be the same as in the case of the category of the part. By the analysis of the endoscope image 100 by the image information assignment unit 72, the first image information of the set category is assigned to the endoscope image 100, and the endoscope image 100 including the designated first image information is set as a selected image.

As described above, in a case where each of the pieces of preset first image information is set in association with at least one of the plurality of categories, it is preferable to designate the first image information for each category. This is because, by setting the category, it is possible to easily and flexibly select the endoscope image 100 according to the user's desire when creating the examination report.

A schema display 105h on the display image setting screen 105 and a schema display 106h on the key image automatic selection screen 106 are fixedly displayed in advance as reference information for a posting position of the examination report 34.

Figure 12:
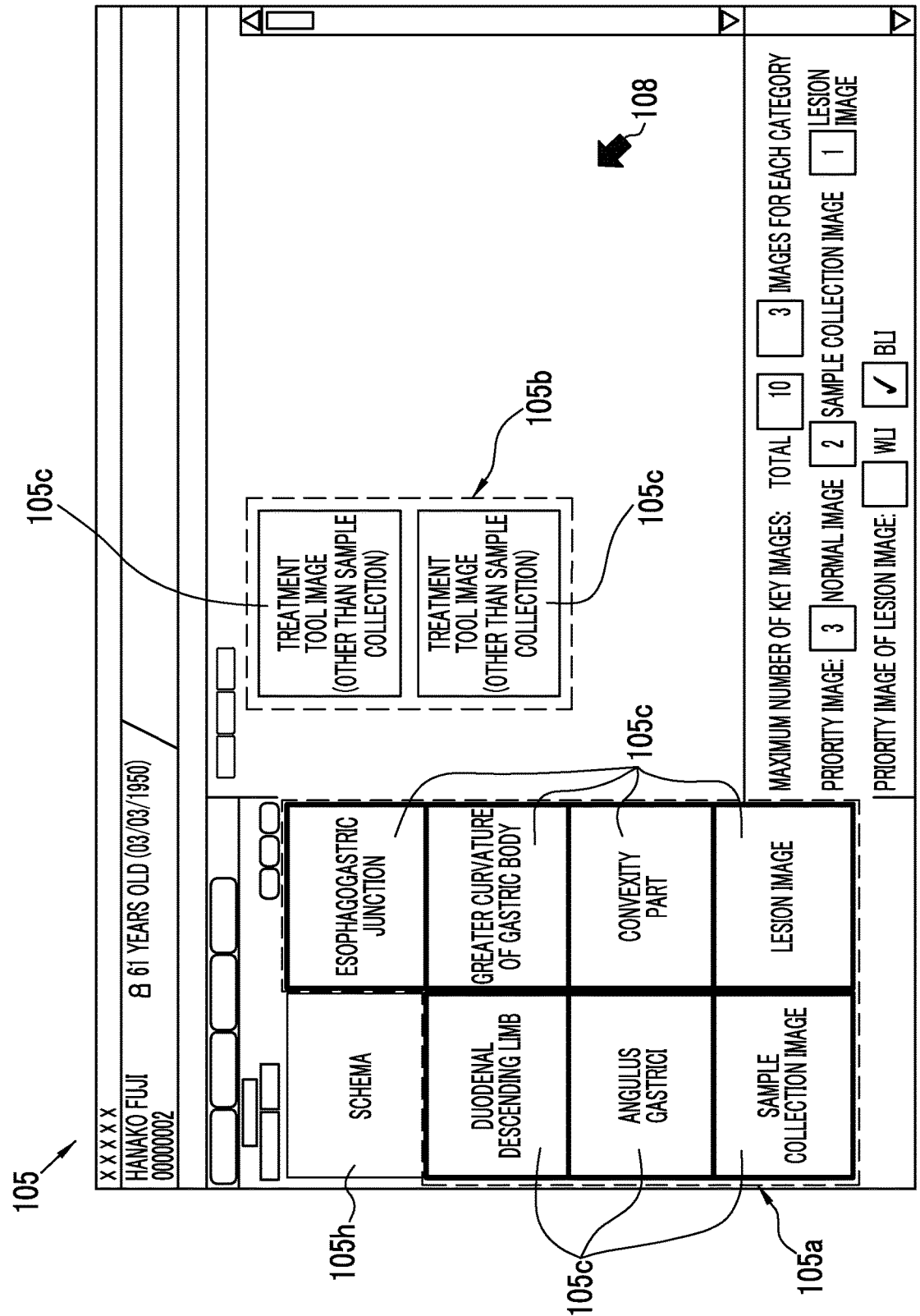
FIG. 12 is an image diagram illustrating a display image setting screen in which a first image information block of another category is moved.

As illustrated in FIG. 12, in the display image setting screen 105, the selection region 105a includes seven types of first image information blocks 105c, and the pieces of first image information designated by the user include five types of parts, a sample collection image, and a lesion image. The user confirms that all the pieces of first image information desired to be the key images are included by the display of the selection region 105a, and ends movement of the first image information block 105c.

Figure 13:
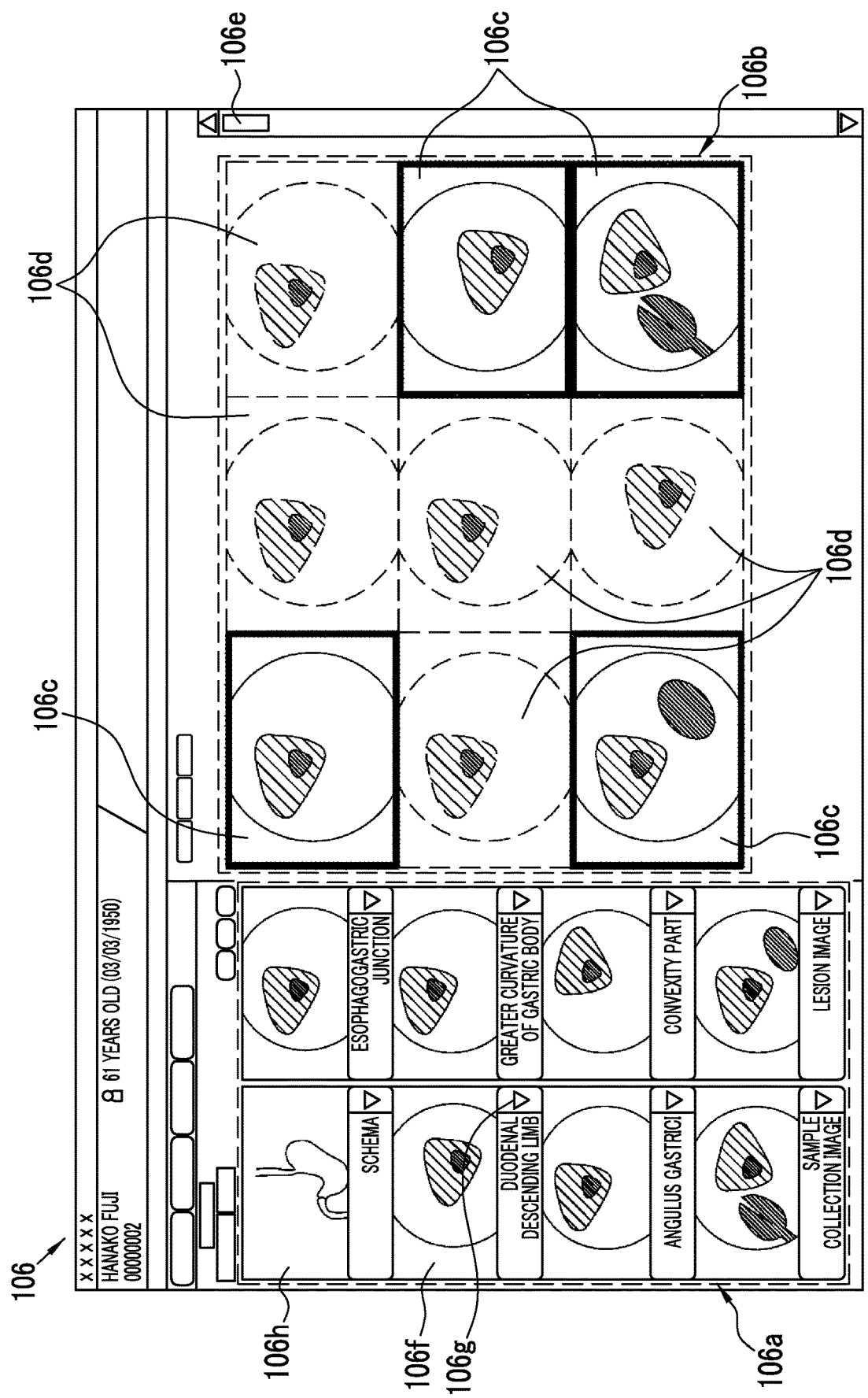
FIG. 13 is an image diagram illustrating a key image automatic selection screen.

The display control unit 74 displays the selected image and the first image information on the display 52 by displaying the key image automatic selection screen 106 (S15). As illustrated in FIG. 13, the selected image 106c is automatically displayed in the selected image display region 106b on the key image automatic selection screen 106 in the selected image display aspect. The selected image display region 106b corresponds to a first display region.

In the present embodiment, the selected image display aspect is preset content, and is a highlight display. Therefore, the selected image 106c is highlighted and displayed in the selected image display region 106b. In the endoscope images 100 acquired in the examination, a non-selected image 106d that is not the selected image 106c is inconspicuously displayed by lightening a color or the like, and the selected image 106c is highlighted. Since an area of the screen is limited, in a case of a size setting for displaying one endoscope image 100, in the selected image display region 106b, all the selected images 106c may not be displayed on one screen. In this case, hidden selected images 106c can be displayed by scrolling the screen of the selected image display region 106b by moving a scroll bar 106e. In this way, in the selected image display aspect, it is preferable to highlight and display the selected image 106c.

In the present embodiment, a setting in which the non-selected image 106d is also displayed in the selected image display region 106b and all of the examination images are displayed is used. On the other hand, a setting in which only the selected image 106c is displayed can be used.

In addition, on the key image automatic selection screen 106, each of the plurality of pieces of first image information is displayed in a selected category display region 106a. The selected category display region 106a corresponds to a second display region. Since the first image information is a part name or the like, the plurality of designated first image information blocks 105c are displayed side by side in the selected category display region 106a together with the part names or the like. The first image information block 105c displays a part name or the like and a representative image of the endoscope image 100 to which the part name or the like is assigned. Therefore, it is possible to recognize the designated part name or the like and the endoscope image 100 to which the part name or the like is assigned at a glance.

Further, since the key image automatic selection screen 106 has the same layout as the display image setting screen 105, the first image information block 105c selected in the selection region 105a on the display image setting screen 105 is similarly displayed in the selected category display region 106a. Therefore, it is possible to easily recognize what kind of image is selected as the key image based on the selected part name.

Figure 14:
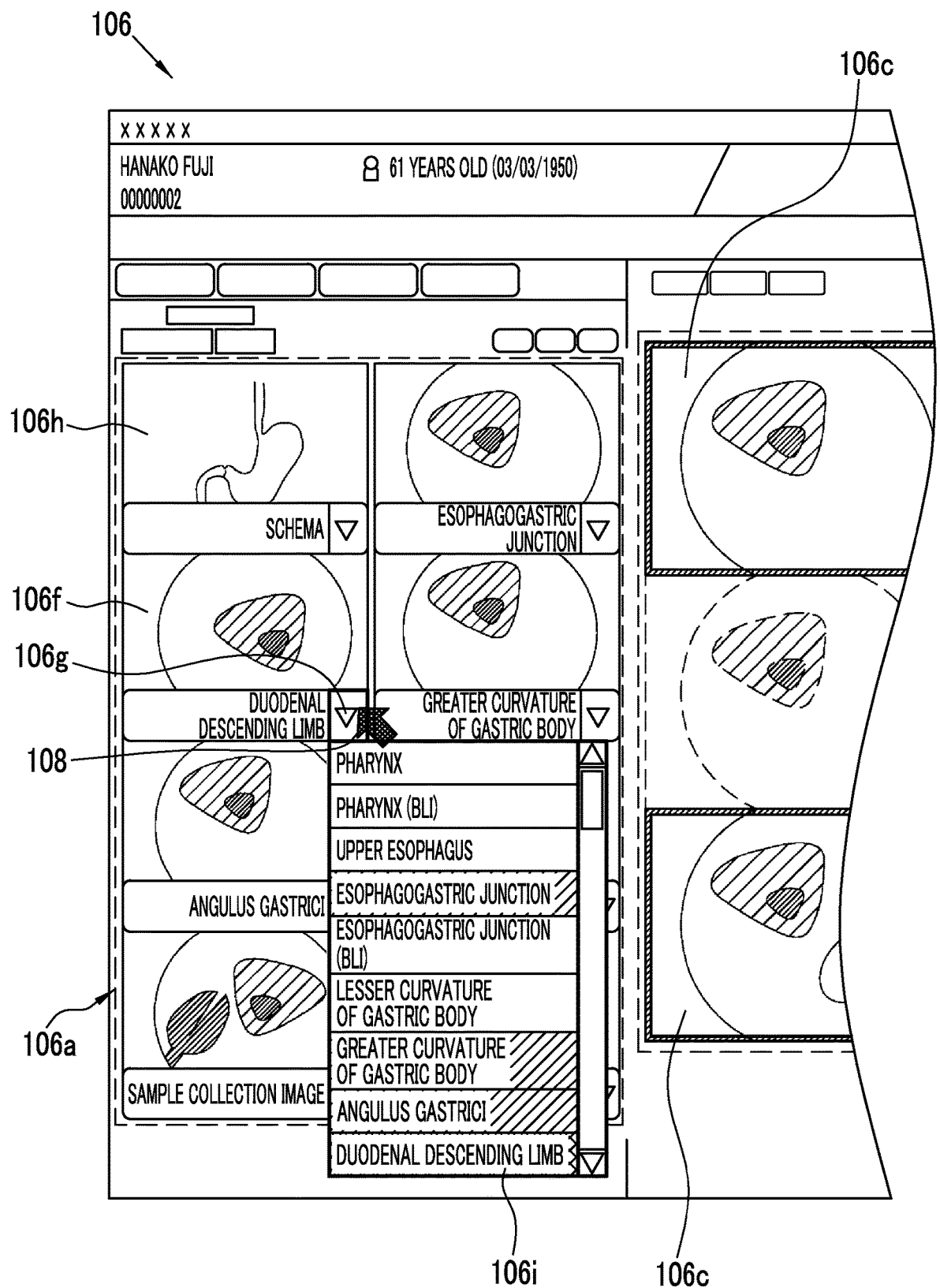
FIG. 14 is an image diagram illustrating a key image automatic selection screen on which a first image information list is displayed.

As illustrated in FIG. 14, in a case where the key image which is the selected image 106c is different from an image desired by the user when the key image automatic selection screen 106 is viewed, the user can click a pop-up button 106g of the first image information block 106f displayed in the selected category display region 106a. In this case, pieces of first image information included in the same category as the category of the first image information block 106f are listed and displayed by a first image information list 106i, and the user can designate the first image information again from the pieces of first image information. In the first image information list 106i, the designated first image information and the non-designated first image information included in the same category are displayed to be different from each other. In addition, the first image information block 106f in which the pop-up button 106g is clicked is highlighted and displayed. The first image information that is previously displayed can be replaced with the first image information clicked on the first image information list 106i. Therefore, in the case of FIG. 14, "duodenal descending limb" can be replaced with the clicked first image information. Alternatively, the first image information may be designated again by clicking a switching button (not illustrated) that is for switching to the display image setting screen 105 and is set in the key image automatic selection screen 106. By repeating these operations, a more optimum key image can be selected.

The user confirms the part names in the selected category display region 106a and all the selected images 106c displayed by scrolling the selected image display region 106b, completes key image selection work, and clicks a completion button (not illustrated) that is set in the key image automatic selection screen 106. Thereby, a report is created. Alternatively, in a case where a report creation button (not illustrated) is pressed, key image selection work is also completed, and a report is created. In a case where key image selection work is completed, various settings of the key image selection used for creating the current report are saved. The saving control unit 75 controls saving of various settings and designations, saving of the endoscope images 100, and saving of the examination report 34.

According to the endoscope image viewing support server 20 which is a medical image processing device configured as described above, the user designates the category of the endoscope image 100 that is the first image information, and thus the key image desired by the user can be automatically selected from a large number of endoscope images 100. Thereby, selection of the key image can be simplified. In addition, the designation is performed on the display screen of the display 52, and thus it is possible to more easily and intelligibly select the key image. In addition, the designation is performed by arbitrarily selecting the first image information, and thus it is possible to flexibly match various key image selection criteria of the user. Thereby, it is possible to select an appropriate key image for each individual user. In addition, the user does not need to confirm a large number of captured endoscope images 100 in selection of the key image, and thus work efficiency of the key image selection is improved.

In addition, the user can confirm the designated first image information and the endoscope image 100 selected as the key image by, for example, the key image automatic selection screen 106 or the like. Thus, it is possible to easily confirm the first image information designated as the key image and the endoscope image 100 selected by the designation. It is also easy to designate the first image information again after the confirmation. Further, by performing the designation a plurality of times, it is possible to automatically select an appropriate key image for the user. Therefore, the endoscope image viewing support server 20 can easily and appropriately select the key image.

Preferably, the display aspect setting unit 91 assigns at least one of a plurality of pieces of preset second image information to the medical image and sets the selected image display aspect based on the second image information. By setting the selected image display aspect based on the second image information, the user can flexibly select the key image by combining the designation of the first image information and the second image information. Thereby, the user can more easily and appropriately select the key image.

The second image information is the same as the first image information, and is assigned to the endoscope image 100 in the same manner as the first image information. Similar to the first image information, the second image information can be information on a part included in the subject image, information on an imaging condition of the medical image, information on a lesion included in the subject image, information on a region-of-interest included in the subject image, or information on a treatment tool included in the subject image.

The image information assignment unit 72 includes a second image information assignment unit 82, and the second image information assignment unit 82 includes a second image information list 84 (refer to FIG. 7). The second image information list 84 included in the second image information assignment unit 82 is the same as the first image information list 83, and is a list in which the second image information is described.

In a case of assigning the second image information, the image information assignment unit 72 assigns, to the endoscope image 100, at least one of the plurality of pieces of second image information which are preset by analyzing the endoscope image 100. Specifically, assignment of the second image information to the endoscope image 100 is realized by adding the second image information to the accessory information 101 included in the imaging information 102, or by adding information indicating that the second image information is included in a case where the second image information is already present in information included in the accessory information 101. A plurality of pieces of second image information may be assigned. In addition, as described above, preferably, the second image information is also set in association with at least one of the plurality of categories, similarly to the first image information.

Which second image information is to be set can be set by the user. For example, by designating the second image information on the display 52 via the display image setting screen 105, the second image information is set. The second image information is an item for selecting and/or rearranging the endoscope image 100 in a case of displaying a selected image on the display 52. Thus, the plurality of pieces of the second image information may be selected and used in combination. As the category of the second image information, preferably, an imaging condition such as illumination light information 101A when the endoscope image 100 is imaged, the presence or absence of a lesion in a case where the endoscope image 100 is analyzed by image processing, the presence or absence of a region-of-interest in a case where the endoscope image 100 is analyzed by image processing, or the presence or absence of a treatment tool in a case where the endoscope image 100 is analyzed by image processing can be used.

In the accessory information 101 included in the imaging information 102 (refer to FIG. 2), the illumination light information 101A indicating one of the imaging conditions indicates a type of illumination light when the endoscope image 100 is imaged. In the present embodiment, the endoscope system 14 includes, as an imaging mode, a normal mode in which white light (WLI) is used as illumination light and a subject is imaged in a natural hue and a special light mode such as blue light (laser) imaging (BLI) in which special light including narrow band light is used as illumination light and an endoscope image 100 in which a specific structure or the like is highlighted is obtained. Therefore, in the illumination light information 101A, a type name of the illumination light, such as "WLI" indicating white light or "BLI" indicating a type of special light, is described.

As in the case of the first image information, in the assignment of the second image information, preferably, the analysis of the endoscope image 100 by image processing is performed by preparing the endoscope image 100 which is determined as including the second image information and performing analysis based on correspondence information in which the endoscope image 100 and the second image information are associated with each other in advance. The correspondence information is the same as in the case of the first image information. Preferably, the correspondence information is a trained model in a machine learning technique. Therefore, for example, in a case where the second image information is the presence or absence of a lesion, analysis of the endoscope image 100 for which it is unknown whether or not the subject image includes a lesion is performed by using a trained model obtained by performing learning using learning data a plurality of times, the learning data being data in which the endoscope image obtained by imaging a subject including a lesion and information on the presence or absence of a lesion such as "including a lesion" are associated with each other. Thereby, whether or not the subject image includes a lesion is obtained as an analysis result. The presence or absence of a region-of-interest or the presence or absence of a treatment tool is also obtained as an analysis result in the same manner.

In a case where a machine learning technique is used, not only a trained model that outputs only the presence or absence of a lesion as an analysis result but also a trained model that analyzes a subject appearing in the endoscope image 100 may be used. From the analysis result of such a trained model, in a case where there is any information that corresponds to the plurality of pieces of preset second image information, the information may be used as the second image information.

Figure 15:
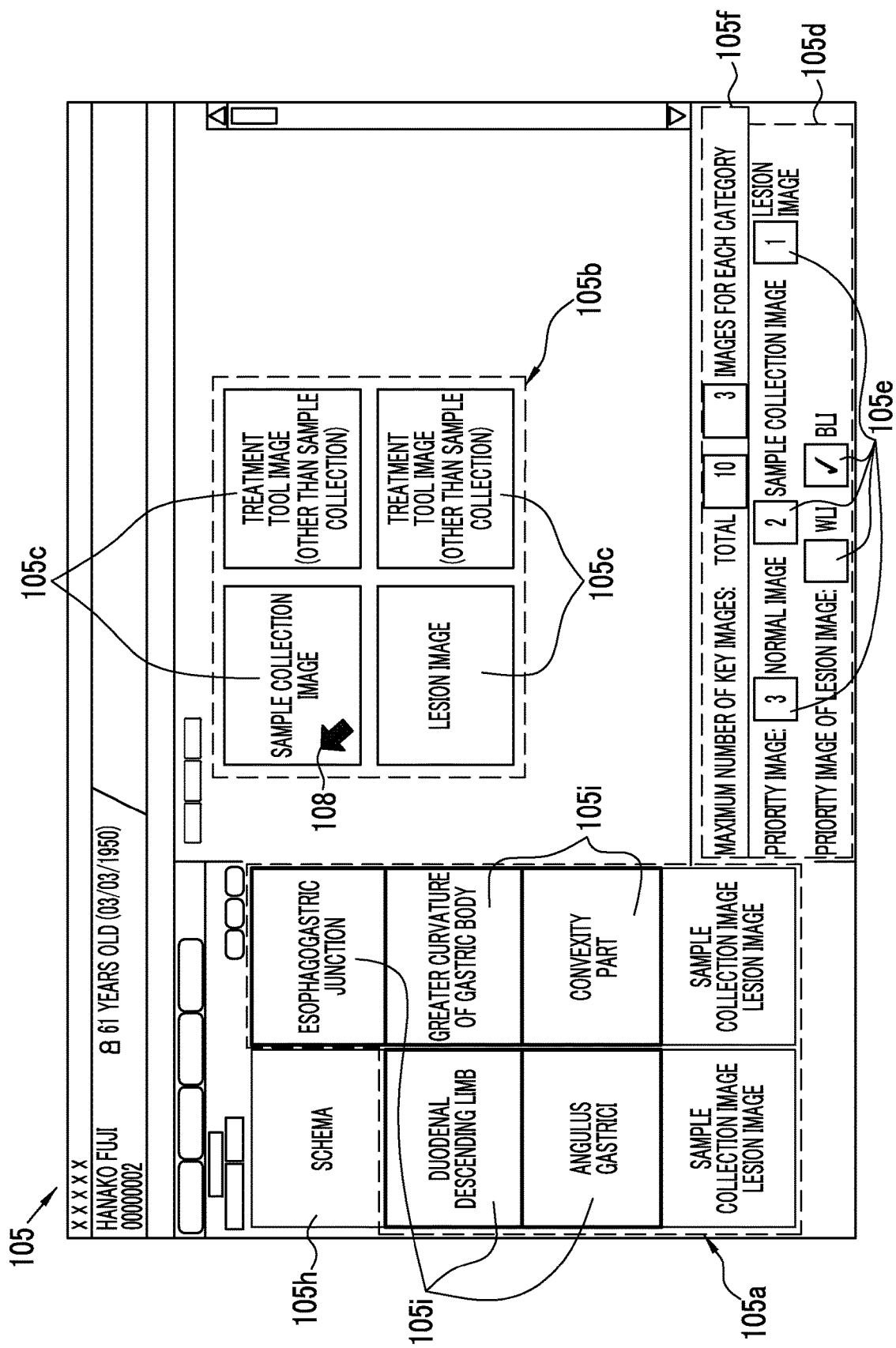
FIG. 15 is an image diagram illustrating a display image setting screen in which a display number is set.

In a case where the first display aspect is set based on the second image information, the first display aspect can be set as follows. As illustrated in FIG. 15, the second image information is set, for example, by a priority image designation region 105d of the display image setting screen 105. As the second image information, the presence or absence of a lesion, the presence or absence of a treatment tool, and an imaging condition are adopted. For the presence or absence of a lesion and the presence or absence of a treatment tool, in the priority image designation region 105d, the user inputs a priority order in an input box 105e such that a lesion image has a first priority, that a sample collection image has a second priority, and that a normal image has a third priority, and selects an imaging condition of BLI by checking an input box 105e for "priority image of lesion image" indicating a priority image in a case of a lesion image. Therefore, in a case of arranging and displaying the selected key images on the display 52 based on the second image information, the first display aspect setting unit 91 sets the first display aspect such that the lesion image, the sample collection image, and the normal image are arranged and displayed in this order and the lesion image which is imaged under an imaging condition of BLI is selected. In a case where the setting on the display image setting screen 105 is completed, the user switches the screen to the key image automatic selection screen 106 by clicking a switching button (not illustrated) that is for switching to the key image automatic selection screen and is included in the display image setting screen 105.

Figure 16:
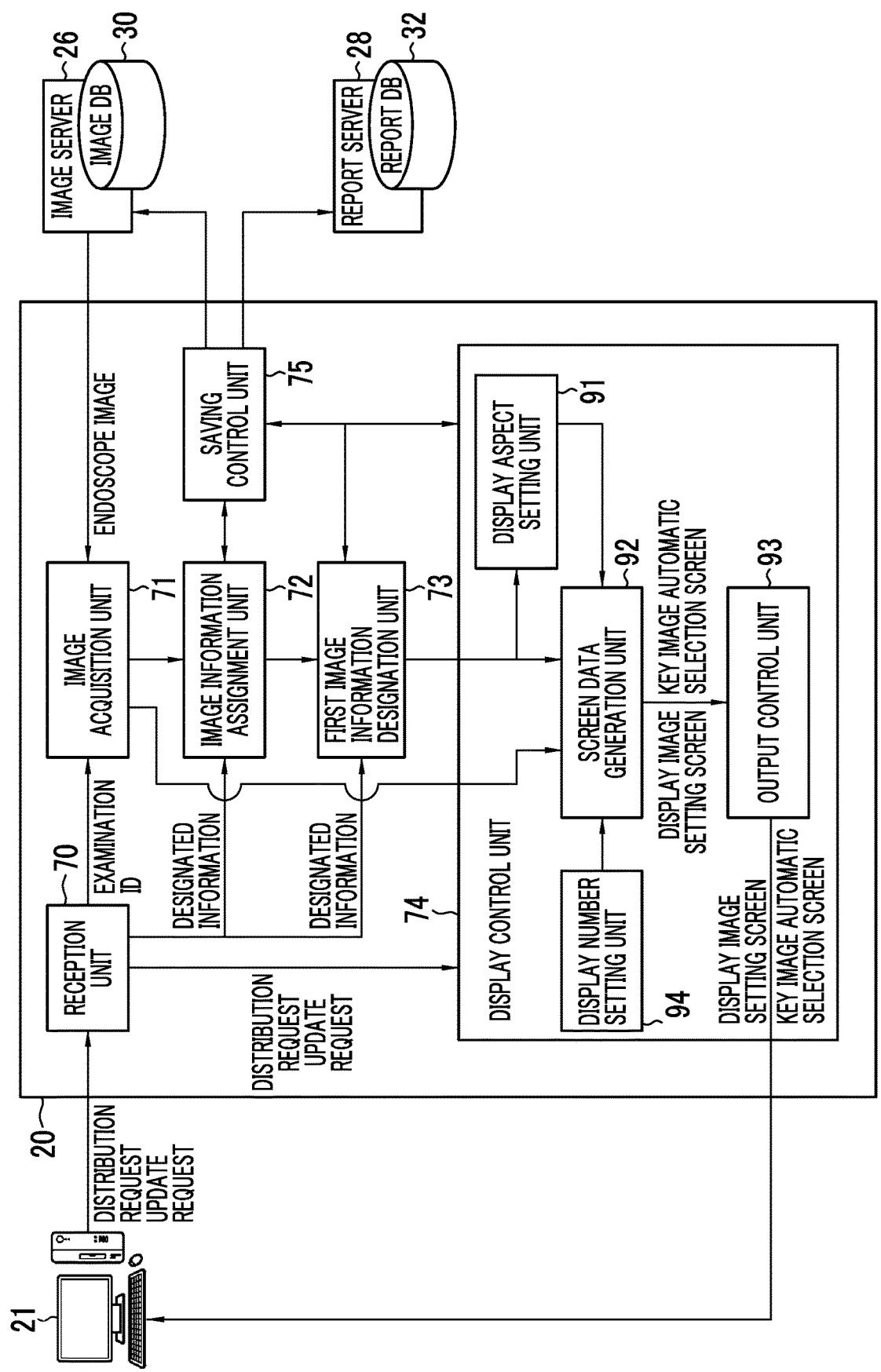
FIG. 16 is an explanatory diagram illustrating an outline of functions of the endoscope image viewing support server including a display number setting unit.

A display number setting unit 94 that sets a maximum number of the selected images 106c to be displayed on the key image automatic selection screen 106 is provided. Preferably, the display control unit 74 performs control of displaying the selected images 106c of which the number is equal to or smaller than the maximum number which is set by the display number setting unit 94 on the key image automatic selection screen 106. As illustrated in FIG. 16, in this case, the endoscope image viewing support server 20 includes the display number setting unit 94. The display number setting unit 94 sets the maximum number of the selected images to be displayed in the selected image display region 106b.

As illustrated in FIG. 15, the maximum number of the selected images to be displayed in the selected image display region 106b of the key image automatic selection screen 106 is set based on the user's setting. The user's setting is set, for example, by inputting a numerical value in a display number setting region 105f of the display image setting screen 105. The maximum number of the selected images is set, for example, by inputting "10" in an input box displayed for "maximum number of key images: total" in the display number setting region 105f. Thereby, the maximum number of the selected images to be displayed in the selected image display aspect is set to 10 in descending order of preset priority. In this case, in a case where the number of the selected images to be displayed in the selected image display aspect is equal to or smaller than 10 before the setting of the number of images to be displayed, the number of images to be displayed is not limited.

In addition, preferably, the display control unit 74 performs control of displaying, on the second display screen, the selected images of which the number is equal to or smaller than the maximum number for each of the pieces of first image information, the maximum number being set by the display number setting unit 94. The setting of the maximum number for each of the pieces of first image information is performed based on the user's setting in the same manner as described above. For example, in the display number setting region 105f, "3" is input to an input box displayed for "for each category", and thus the maximum number is set. Thereby, the maximum number of the selected images to be displayed in the selected image display aspect is 3 for each part which is the first image information in descending order of priority. In the same manner as described above, in a case where the number of the selected images to be displayed in the selected image display aspect is equal to or smaller than 3 before the setting of the number of images to be displayed, the number of images to be displayed is not limited.

As illustrated in FIG. 17, a display setting saving unit 95 that saves designations and settings performed by at least one of the first image information designation unit 73, the display aspect setting unit 91, and the display number setting unit 94 as display settings is provided. Preferably, the display control unit 74 displays the endoscope images 100 on the second display screen based on the display settings. As illustrated in FIG. 17, the saving control unit 75 includes a display setting saving unit 95. As described above, key image automatic selection is performed based on the designations and the settings by the first image information designation unit 73, the display aspect setting unit 91, and the display number setting unit 94. By using these combinations, a setting for key image automatic selection can be performed in detail for each individual user. Therefore, in a case where the setting is saved as the display setting, when the user desires to perform key image automatic selection at the next time with the same setting, it is possible to perform key image automatic selection with the same setting by searching for and loading the saved display setting. Therefore, it is possible to load the saved display setting for key image automatic selection by a simple method, and thus it is possible to save extra time and effort.

As illustrated in FIG. 18, in a display setting 96, for example, for the designation of the first image information designation unit 73, "esophagogastric junction, duodenal descending limb, greater curvature of gastric body, angulus gastrici, convexity part" is designated. In the setting of the display aspect setting unit 91, for "priority image", "1 lesion image, 2 sample collection image, 3 normal image" is set, and for "priority image of lesion image", "BLI" is set. In the setting of the display number setting unit 94, for "maximum number of key images", "total 10" and "3 for each category" are set. These designations and settings are collectively saved as first display setting.

Preferably, the display setting is saved for each user. It is preferable to save the display setting for each user because it is not necessary to set a detailed setting for each user each time examination is performed.

In addition, it is preferable to save the display setting for each user group including a plurality of users.

The user group including the plurality of users is, for example, each medical department in a medical facility or each medical facility. Therefore, it is possible to save the display setting of the key image automatic setting for each medical department or each medical facility.

In addition, it is preferable to save the display setting for each purpose of imaging. Examples of the purpose of imaging include a screening examination, a detailed examination of a polyp, a treatment using a treatment tool, and the like. For example, in a screening examination, by calling the display setting in the screening examination, it is possible to display the key image setting screen on which optimum key images in the screening examination are automatically displayed without taking time and effort.

In the embodiment, as a hardware structure of a processing unit that executes various processing, such as the reception unit 70, the image acquisition unit 71, the image information assignment unit 72, the first image information designation unit 73, the display control unit 74, and the saving control unit 75 which are included in the endoscope image viewing support server 20 as a medical image processing device, the following various processors may be used. The various processors include a central processing unit (CPU) which is a general-purpose processor that functions as various processing units by executing software (program), a programmable logic device (PLD) such as a field programmable gate array (FPGA) which is a processor capable of changing a circuit configuration after manufacture, a dedicated electric circuit which is a processor having a circuit configuration specifically designed to execute various processing, and the like.

One processing unit may be configured by one of these various processors, or may be configured by a combination of two or more processors having the same type or different types (for example, a plurality of FPGAs or a combination of a CPU and an FPGA). Further, the plurality of processing units may be configured by one processor. As an example in which the plurality of processing units are configured by one processor, firstly, as represented by a computer such as a client and a server, a form in which one processor is configured by a combination of one or more CPUs and software and the processor functions as the plurality of processing units is adopted. Secondly, as represented by a system on chip (SoC) or the like, a form in which a processor that realizes the function of the entire system including the plurality of processing units by one integrated circuit (IC) chip is used is adopted. As described above, the various processing units are configured by using one or more various processors as a hardware structure.

Further, as the hardware structure of the various processors, more specifically, an electric circuit (circuitry) in which circuit elements such as semiconductor elements are combined is used.

The present invention can also be used, in addition to an endoscope system, a processor device, and other related devices that acquire an endoscope image, a system or a device that acquires a medical image (including a moving image) other than the endoscope image. For example, the present invention can be applied to an ultrasound examination device, an X-ray imaging device (including a computed tomography (CT) examination device, a mammography device, and the like), a magnetic resonance imaging (MRI) device, and the like.

EXPLANATION OF REFERENCES

10: endoscope image viewing support system
12, 24: network
14: endoscope system
15: endoscope
16: light source device
17: processor device
18: display
19: keyboard
20: endoscope image viewing support server
20D: display
21: client terminal
22: server group
26: image server
28: report server
30: image database
32: report database
34: examination report
34A: report body
40: CPU
42: memory
44: storage device
46: communication I/F
48: input/output unit
50: data bus
52: display
54: input device
56: application program
58: start screen
58A: ID input field
58B: confirmation button
60: GUI control unit
62: request issuing unit
70: reception unit
71: image acquisition unit
72: image information assignment unit
73: first image information designation unit
74: display control unit
75: saving control unit
81: first image information assignment unit
82: second image information assignment unit
83: first image information list
84: second image information list
91: display aspect setting unit
92: screen data generation unit
93: output control unit
94: display number setting unit
95: display setting saving unit
96: display setting
100: endoscope image
100S: key image
101: accessory information
101A: Illumination light information
102: imaging information
103: report display screen
104: opinion
105: display image setting screen
105a: selection region
105b: non-selection region
105c, 106f: first image information block
105d: priority image designation region
105e: input box
105f: display number setting region
105h, 106h: schema display
106: key image automatic selection screen
106a: selected category display region
106b: selected image display region
106c: selected image
106d: non-selected image
106e: scroll bar
106g: pop-up button
106i: first image information list
108: pointer
S11 to S15: step

What is claimed is:

1. A medical image processing device comprising:
a processor configured to:
acquire a plurality of medical images including a subject image;
assign at least one of a plurality of pieces of first image information which are preset to the medical images by analyzing the medical images;
perform designation of at least one of the plurality of pieces of first image information; and
perform control of displaying a selected image in a first display region of an image display screen in a selected image display aspect, the selected image being the medical image to which the designated first image information is assigned among the plurality of medical images, and perform control of displaying each of the plurality of pieces of designated first image information as text information in a second display region of the image display screen,
wherein the designated first image information is information on a part included in the subject image, information on an imaging condition of the medical image, information on a lesion included in the subject image, information on a region-of-interest included in the subject image, or information on a treatment tool included in the subject image.

2. The medical image processing device according to claim 1,
wherein the processor is configured to:
assign at least one of a plurality of pieces of second image information which are preset to the medical images by analyzing the medical images; and
set the selected image display aspect based on the second image information.

3. The medical image processing device according to claim 2,
wherein each of the plurality of pieces of second image information which are preset is set in association with at least one of a plurality of categories.

4. The medical image processing device according to claim 1,
wherein each of the plurality of pieces of first image information which are preset is set in association with at least one of a plurality of categories, and
the processor is configured to perform the designation for each of the categories.

5. The medical image processing device according to claim 3, wherein the category is at least one of information on the part included in the subject image, information on the imaging condition of the medical image, information on the lesion included in the subject image, information on the region-of-interest included in the subject image, or information on the treatment tool included in the subject image.

6. The medical image processing device according to claim 4,
wherein the processor is configured to:
perform control of displaying the plurality of pieces of first image information in a third display region of the image display screen for each of the categories; and
perform the designation based on a user's selection of the plurality of pieces of first image information displayed in the third display region.

7. The medical image processing device according to claim 1,
wherein the processor is configured to:
set a maximum number of the selected images to be displayed in the first display region; and
perform control of displaying the selected images of which the number is equal to or smaller than the set maximum number in the first display region.

8. The medical image processing device according to claim 1,
wherein the processor is configured to perform an analysis based on first correspondence information in which the medical image including the first image information and the first image information are associated with each other in advance.

9. The medical image processing device according to claim 5,
wherein the processor is configured to perform an analysis based on second correspondence information in which the medical image including the second image information and the second image information are associated with each other in advance.

10. The medical image processing device according to claim 1,
wherein designation performed by the processor is saved as a display setting, and
the selected images are displayed on the image display screen based on the display setting.

11. The medical image processing device according to claim 10,
wherein the display setting is saved for each of users.

12. The medical image processing device according to claim 11,
wherein the display setting is saved for each user group including a plurality of the users.

13. The medical image processing device according to claim 10,
wherein the display setting is saved for each purpose of the imaging.

14. An operation method of a medical image processing device, the method comprising:
an image acquisition step of acquiring a plurality of medical images including a subject image obtained by imaging;
an image information assignment step of assigning at least one of a plurality of pieces of first image information which are preset to the medical images by analyzing the medical images;
a first image information designation step of performing designation of at least one of the plurality of pieces of first image information; and
a display control step of performing control of displaying a selected image in a first display region of an image display screen in a selected image display aspect, the selected image being the medical image to which the designated first image information is assigned among the plurality of medical images, and performing control of displaying each of the plurality of pieces of designated first image information as text information in a second display region of the image display screen,
wherein the designated first image information is information on a part included in the subject image, information on an imaging condition of the medical image, information on a lesion included in the subject image, information on a region-of-interest included in the subject image, or information on a treatment tool included in the subject image.

15. A non-transitory computer readable medium for storing a computer-executable program for causing a computer to function as a medical image processing device, the program causing a computer to execute:

an image acquisition function of acquiring a plurality of medical images including a subject image obtained by imaging;

an image information assignment function of assigning at least one of a plurality of pieces of first image information which are preset to the medical images by analyzing the medical images;

a first image information designation function of performing designation of at least one of the plurality of pieces of first image information; and a display control function of performing control of displaying a selected image in a first display region of an image display screen in a selected image display aspect, the selected image being the medical image to which the designated first image information is assigned among the plurality of medical images, and performing control of displaying each of the plurality of pieces of designated first image information as text information in a second display region of the image display screen, wherein the designated first image information is information on a part included in the subject image, information on an imaging condition of the medical image, information on a lesion included in the subject image, information on a region-of-interest included in the subject image, or information on a treatment tool included in the subject image.

* * * * *